United States Patent [19]

Sugerman et al.

[11] Patent Number: 4,623,738
[45] Date of Patent: Nov. 18, 1986

[54] NEOALKOXY ORGANO-TITANATES AND ORGANO-ZIRCONATES USEFUL AS COUPLING AND POLYMER PROCESSING AGENTS

[75] Inventors: Gerald Sugerman, Allendale, N.J.; Salvatore J. Monte, Staten Island, N.Y.

[73] Assignee: Kenrich Petrochemicals, Inc., Bayonne, N.J.

[21] Appl. No.: 725,437

[22] Filed: Apr. 22, 1985

Related U.S. Application Data

[63] Continuation-in-part of Ser. No. 609,727, May 14, 1984, and a continuation-in-part of Ser. No. 651,119, Sep. 14, 1984.

[51] Int. Cl.$^4$ ............................................. C07F 7/28
[52] U.S. Cl. .................... 556/17; 523/200; 523/202; 523/215; 524/108; 524/128; 556/24; 556/54; 556/55; 556/56; 106/288 R; 106/288 Q; 106/308 Q
[58] Field of Search ............ 556/17, 24, 54, 55, 556/56; 260/414; 523/200, 202, 215, 508, 515; 524/108, 128; 106/288 Q, 288 R, 308 Q

[56] References Cited

U.S. PATENT DOCUMENTS

| | | |
|---|---|---|
| 3,119,852 | 1/1964 | Gilsdorf . |
| 3,354,189 | 11/1967 | Revuleas . |
| 3,403,176 | 9/1968 | Block et al. . |
| 3,772,355 | 11/1973 | Merz . |
| 4,069,192 | 1/1978 | Monte et al. . |
| 4,080,353 | 3/1978 | Monte et al. . |
| 4,087,402 | 5/1978 | Monte et al. . |
| 4,094,853 | 6/1978 | Monte et al. . |
| 4,098,758 | 7/1978 | Monte et al. . |
| 4,122,062 | 10/1978 | Monte et al. . |
| 4,137,183 | 1/1979 | Caspari . |
| 4,192,792 | 3/1980 | Sugerman et al. . |
| 4,277,415 | 7/1981 | Sugerman et al. . |
| 4,287,131 | 9/1981 | Langer et al. . |
| 4,360,474 | 11/1982 | Brady et al. . |
| 4,374,760 | 2/1983 | Charles . |

FOREIGN PATENT DOCUMENTS

1091525 11/1967 United Kingdom .

OTHER PUBLICATIONS

Chemical Abstracts, 67, 74269z (1967).
Chemical Abstracts, 88, 137940t, 191974v and 38478s (1978).
Chemical Abstracts, 89, 130205u and 111396r (1978).
Chemical Abstracts, V 79, 78093h (1973).
Chemical Abstracts, 86, 56110d (1977).
Chemical Abstracts, 87, 85699d (1977).

*Primary Examiner*—Helen M. S. Sneed
*Attorney, Agent, or Firm*—Bert J. Lewen; Henry Sternberg

[57] ABSTRACT

A composition of matter comprising neoalkoxy compounds having the following formula:

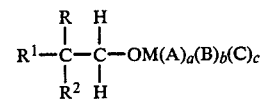

wherein M is titanium or zirconium, R, $R^1$ and $R^2$ are each a monovalent alkyl, alkenyl, alkynyl, aralkyl, aryl or alkaryl group having up to twenty carbon atoms or a halogen or ether substituted derivative thereof, and, in addition, $R^2$ may also be an oxy derivative or an ether substituted oxy derivative of said groups; A, B, and C are each a monovalent aroxy, thioaroxy, diester phosphate, diester pyrophosphate, oxyalkylamino, sulfonyl or carboxyl containing up to 30 carbon atoms; and $a+b+c=3$.

18 Claims, No Drawings

NEOALKOXY ORGANO-TITANATES AND ORGANO-ZIRCONATES USEFUL AS COUPLING AND POLYMER PROCESSING AGENTS

CROSS-REFERENCE TO RELATED APPLICATIONS

This is a continuation-in-part of U.S. patent applications Ser. No. 609,727 filed May 14, 1984 and Ser. No. 651,119 filed Sept. 14, 1984.

BACKGROUND OF THE INVENTION

The use of monoalkoxy organo-titanates, i.e., those containing primary, secondary or tertiary alkoxy groups directly attached to titanium, as coupling agents for particulate material and polymeric resins is well known. See U.S. Pat. No. 4,122,062. While these materials have proven effective, they could not be used directly where the polymeric systems required compounding at temperatures substantially in excess of 200° C., because these known organo-titanates had insufficient thermal and/or solvolytic stability. Accordingly, with such compounds it was necessary to first mechanically preblend at temperatures below 200° C. in advance of polymeric resin compounding above 200° C. This two-step process, which is also necessary with other coupling agents, e.g., silanes, alumino- zirconates and aluminates, is both costly and time-consuming, requiring the use of special equipment.

Furthermore, the known alkoxy titanates have exhibited poor performance because of their relatively low stability in the presence of certain solvents, particularly water at elevated temperatures. This drawback has made these organo-titanates ineffective for applications requiring long periods of storage stability in proton-containing solvents, such as alcohols and ketones and in ester plasticizers.

BRIEF DESCRIPTION OF THE INVENTION

It has now been discovered that neoalkoxy organo-titanates and organo-zirconates, a new groups of compounds, overcome both of the above-mentioned deficiencies and, in addition, enhance the performance of polymer matrices whether or not they contain particulate. This latter effect relates to the ability of these novel neoalkoxy organo-titanates and organo-zirconates to remain stable at elevated temperatures, i.e., over 200° C., for a sufficient period in processing equipment used to form high temperature polymers. This stability, particularly in high shear systems, permits the interaction of the titanate or zirconates with the polymer during polymerization, so as to alter the rheological characteristics associated with such processing. The exact mode of performance enhancement is, as yet, incompletely understood, but is believed to involve wall shear reduction, antioxidant and/or polymer component rearrangement activity. It is certain, however, that the special structure associated with the neoalkoxy group provides sufficient thermal and solvolytic stabilization to permit the novel materials to be employed in selected areas where the prior art organo-titantes, because of their instability, were non-functional or degraded the performance characteristics of the polymer compositions.

The neoalkoxy zirconates are particularly useful for peroxide-cured and air-cured systems, since they accelerate the polymerization reaction. On the other hand, the titanates (because of their tendency to oxidize free radicals) inhibit such polymerizations. Hence, the neoalkoxy zirconates most unexpectedly provide a means of both coupling filler to the polymer and accelerating the polymerization.

In addition, the neoalkoxy zirconates give polymer composites having most beneficial thixotropic properties; that is, such materials exhibit low viscosity under high shear and high viscosity under low shear. This is most beneficial since the low viscosity under high shear facilitates spraying and other applications of the polymeric material, while the high viscosity/low shear (as for example under storage conditions) prevents settling and enhances the shelf life of such polymers. A still further advantage of the organo-zirconates is their ability to maintain their coupling capability even in the presence of moisture. This is of substantial importance in the case of fiberglas-reinforced unsaturated polyesters. Silanes, on the other hand, cannot be used in such applications because of their adverse effect on processability. Isocyanates such as thixotropes in such applications suffered from the problems of toxicity and sensitivity to moisture.

The organo-zirconates are also outstanding in silicon resin applications, since they are most effective in bonding silicon resin to glass.

DETAILS OF THE INVENTION

The subject invention relates to novel neoalkoxy organo- titanium which may be represented by the formula:

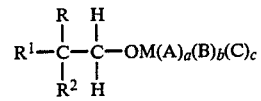

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative of said groups. The various R, $R^1$ and $R^2$ may each contain up to three ether oxygen or halogen substituents, provided the total number of carbon atoms for each such R group does not exceed 20, inclusive of the carbon atoms contained in substituent portions. A, B and C may be an aroxy (ArO—), thioaroxy (ArS—), diester phosphate $((R^3O)(R^4O)P(O)O-)$, diester pyrophosphate $((R^3O)(R^4O)P(O)OP(O))$, oxyalkylamino $(R^5R^6NR^7O-)$, sulfonyl $(ArS(O)_2O-)$, or carboxyl $(RC(O)O-)$. Each group may contain up to 30 carbon atoms.

Ar, in the above formulas, may be a monovalent aryl or alkaryl group having from 6 to about 20 carbon atoms, optionally containing up to 3 ether oxygen substituents, and substituted derivatives thereof wherein the substitutions are up to a total of three halogens or amino groups having the formula $NR^8R^9$ wherein $R^8$ and $R^9$ are each hydrogen, an alkyl group having 1 to 12 carbon atoms, an alkenyl group having from 2 to 8 carbon atoms, a cycloalkyl group having from 3 to 12 carbon atoms, and an aryl group having from 6 to 12 carbon atoms; and $R^3$ and $R^4$ may each be the same group as R, $R^1$ and Ar. $R^5$ and $R^6$ may be hydrogen, an alkyl or aminoalkyl group having from 1 to 15 carbon atoms and $R^7$ may be an alkylene group having from 1 to 6 carbon atoms or an arylene group having from 6 to 10 carbon atoms or a combination thereof; and $a+b+c$ is equal to 3.

A wide variety of ligands, subject to the limitations heretofore expressed, may be used in the practice of the invention. The most suitable for a particular application will depend largely upon the polymer system employed and, to a lesser degree, upon the particular curative and/or extenders introduced into such system, if any.

Particularly preferred examples of the R, $R^1$ and $R^2$ groups are alkyl having 1 to 8 carbon atoms; aralkyl having 6 to 10 carbon atoms such as benzyl; the aryl and alkaryl groups having from 6 to 10 carbon atoms including phenyl, naphthyl, tolyl, xylyl; and the halogen-substituted bromophenyl; and the allyloxy-substituted alkyl having from 4 to 20 carbon atoms and the allyloxy-substituted aryl having from 9 to 20 carbon atoms. Where $R^2$ is an oxy derivative, the most preferred compounds are the alkoxy derivatives having from 1 to 3 carbon atoms and the phenoxy group.

Preferred $R^3$ and $R^4$ groups are alkyl groups having 1 to 12 carbon atoms, aryl and alkaryl groups having from 6 to 12 carbon atoms and ether-substituted alkyl having from 3 to 12 carbon atoms.

Examples of specific R, $R^1$, $R^2$, $R^3$ and $R^4$ groups are: methyl, propyl, cyclohexyl, 2,4-dimethoxybenzyl, 1-methyl-4-acenaphthyl-2-ethyl-2-furyl and methallyl. $R^2$, in addition, may be methoxy, phenoxy, naphthenoxy, cyclohexene-3-oxy, 4-isobutyl-3-methoxy, 1-phenanthroxy and 2,4,6-trimethylphenoxy.

Examples of A, B and C ligands useful in the practice of this invention are likewise numerous. These include aryl and thioaryl ligands such as phenoxy, 2,4-dimethyl-1-naphthoxy, 3-octyl-1-phenanthroxy and 3,5-diethyl-2-thioanthryl and 2-methyl-3-methoxy thiophenyl as well as diester phosphates such as dibutyl, methylphenyl, cyclohexyl, lauryl and bismethoxyethoxyethyl phosphate and their pyrophosphate analogs as well as aryl sulfonyl groups such as phenylsulfonyl, 2,4-dibutyl-1-naphthalene sulfonyl and 2-methyl-3-ethyl-4-phenanthryl sulfonyl.

Particularly effective are carboxyl groups such as acetyl, methacryl, stearyl, 4-phenoxy and 4-phenoxy butyl. Illustrative of the compounds of the instant invention are those listed in Table A:

can be used to prepare compositions of the invention. These are illustrated in Examples A through C.

In the first process, shown in Example A, one mole of an alcohol of the formula $RR^1R^2CCH_2OH$ (the hydrophilic precursor) is reacted with 3 moles of a compound of the formula $H(A)_a(B)_b(C)_c$ (the hydrophobic precursor) and one mole of titanium or zirconium tetrachloride. The reaction may take place in the presence of a solvent such as xylene at temperature of from $-20°$ C. to $140°$ C. Hydrogen chloride gas is involved.

A second method which may be used is described specifically in Example B. Here a tetraalkoxy titanate or zirconate is substituted for the titanium tetrachloride. Here the reaction is carried out at a temperature of from $0°$ C. to $200°$ C. During the course of the reaction four moles of alcohol, corresponding to the alkoxy groups on the titanium or zirconium compound, are evolved. It will be understood that in the foregoing reactions one or more hydrophobic precursors may be used to form the neoalkoxy compound.

The third method of the invention involves the admixture of two titanate or zirconate compounds, the first containing four neoalkoxy hydrophilic radicals and the second containing four hydrophobic radicals. By mixing one mole of the former with three moles of the latter a reaction product having the structure of the neoalkoxy compounds of the invention can be obtained. This procedure is generally carried out in the presence of a solvent such as toluene at a temperature of $0°$ C. to $150°$ C.

In addition to the neoalkoxy compounds, the instant invention also relates to compositions containing the neoalkoxy compounds and polymers, particulate material treated with the neoalkoxy compounds, and blends of polymers, particulate material and the neoalkoxy compounds.

Even a small amount of the neoalkoxy compounds markedly affects the rheological properties of polymers and therefore makes these compounds useful as processing aids. The interaction between the external surfaces and the polymer can be measured by melt flow index. As is well known to the art, flow characteristics of the

TABLE A $(CH_3)_3CCH_2OTi[OC(O)C_{17}H_{35}]_3,(CH_3)_2(C_6H_5)CCH_2OTi(OC_6H_5)_2[OC(O)C_6H_5]$
$(CH_3=C(CH_3)CH_2O)_2(C_2H_5)CCH_2OTi[2SC_6H_4—N—3C_2H_5]_2[OC_6H_4C(CH_3)_2C_6H_5]$
$(C_6H_{11}O)(iso-C_{12}H_{25})_2CCH_2OTi[OS(O)_2C_6H_4C_{12}H_{25}]_3$
$(CH_2=CHCH_2O)(C_3H_7)(C_2H_5)CCH_2OTi[OP(O)(OC_4H_9)OP(O)(OH)OC_4H_9)]_3$
$(CH_3)(HC=CCH_2O)(C_6H_5)CCH_2OTi[OP(O)(OC_2H_4OCH_3)(OCH_3)]_2[OC_6H_4—p-C_2H_5]$
$(C_6H_{11})(iso-C_3H_7)(C_4H_9O)CCH_2OTi[S(O)_2C_6H_4—O—CH_3][SC_6H_5]_2$
$(CH_3)(C_6H_5CH_2O)(C_2H_5)CCH_2OTi[OP(O)(OC_6H_4—p-CH_3)(O)(C_2H_4)(OCH_3)]$
$[OP(O)(OH)OP(O)(OC_3H_7)_2]_2$
$(C_2H_5)(C_3H_7)(CH_2=CHO)CCH_2OTi[OC(O)neo-C_9H_{17}]_3$
$[C(CH_3)_2=C(C_6H_5)OCH_2]_2(iso-C_3H_7)CCH_2OTi[OC_{10}H_7][OC(O)CH_2CH_3]_2$
$(C_2H_5OCH_2)(CH_3)(CH_3)(C_6H_5)CCH_2OTi[OC_2H_4NHCH_3]_3$
$(CH_3)_2(C_4H_9)CCH_2OTi[OC_3H_6N(C_6H_5)C_4H_8C_{10}H_7]_2[OC(O)CH_3]$
$(C_6H_5)_2(CH_3O)CCH_2OZr[OC(O)C_9H_{19}—neo]_3$
$(C_{10}H_7S)(C_3H_5)(C_2H_5)CCH_2OZr(OC_6H_4Cl)[SC_6H_3CCH_3)_2](OS(O)_2C_{10}H_9—2)$
$(CH_3)_2(C_5H_{11}O)(CCH_2OZr[SC_6H_4C(CH_3)_2C_6H_5]_3$
$(CH_2=CH)_2(CH_3OCH_2)CCH_2OZr[OP(O)(OC_6H_5Br)_2][OP(O)(OCH_3)OP(O)(OCH_3)(OH)]_2$
$(C_3H_7OCH_2O)(C_2H_5)(CH_3)CCH_2OZr[OC_6H_5]_3$
$(CH_3)_3CCH_2OZr[OC(O)CH_3][OP(O)(OC_5H_9)(OCH_2C_6H_7CH_3)]$
$[OS(O)_2C_6H_3(Cl)(Br)(CH_3)—1,2,3]$ As in the case of the materials in the prior art, the organo-titanates and organo-zirconates are useful as coupling agents because the alkoxy portion is a hydrophilic group capable of reacting with filler material and the A, B and C groups are hydrophobic and capable of reacting with organic material. A variety of processes resin are particularly important during processing and shaping of the polymers, as for example by extrusion or injection molding.

While a wide variety of polymers may be treated with the neoalkoxy compounds of the invention, the admixture thereof are particularly useful with engineering plastics, which are conventionally processed between 200° and 400° C. The organo-titanates of the prior art were not satisfactory in this application, because of their lack of stability. It should be understood, however, that the neoalkoxy compounds may also be blended with other resins such as PVC and used in paint and other coating applications, in the latter cases because of the solvent stability of these compounds.

Broadly, from 0.005 to 5 wt. % of the neoalkoxy compounds are added to the resin, preferably from 0.1 to 1.0%. If the amount of the neoalkoxy compound added is greater than that needed to affect the surface properties of the resin, the neoalkoxy compounds will have a plasticizing effect on the resin.

The optimum amount of the neoalkoxy compounds added to the resins may be readily determined by those skilled in the art by consideration of the examples set forth herein and by simple experimentation. By so proceeding, the desired flow properties for a particular resin can be reasily achieved.

Examples of the engineering plastics which may be admixed with neoalkoxy compounds include epoxy resins, fluorocarbons, modified phenylene oxides, nylons, polyethylene terephthalate, polybutylene terephthalates, phenolics, polyamides, polycarbonates, polyetheretherketones, polyaryletherketones, polyether imides, polyphenylene sulfides, polysulfones, polyarylsulfones, styrene, polyester copolymers, styrenics, such as, polystyreneacrylonitrile-butadiene-styrene, styrene-actylonitrile, styrene-butadiene, and styrene-maleic anhydride copolymers.

The neoalkoxy compounds also improve the dimensional stability of shaped resins. This is reflected by reduced water absorption in humid environments, and is amply demonstrated by the examples hereinafter set forth. Other positive effects in certain filled plastics include improved conductivity, a reflection of the improved dispersion of the conductive filler in the polymer; flame retardancy, a result of the exclusion of air from the interstices of the resin and better filler dispersion; less heat distortion; and catalytic effects. Data for all of these effects are given in the examples which follow.

The solvent stability of the neoalkoxy compounds, as mentioned previously, is also a marked advantage over the prior art. The prior art hydrolyzable groups reacted with many solvents, thereby destroying the efficacy of the organo-titanate as a coupling agent. Examples of solvents which quickly deactivated the prior art coupling agents are protonated solvents, such as hydroxylated polymers, vicinal glycols (both monomeric and polymeric), solvents which exhibit keto-enol tautomerism, organic acids, esters, isocyanates and carboxylates. In the case of the neoalkoxy compounds of the invention, however, they are substantially non-reactive at the processing temperatures of most polymeric materials.

The resistance to protonated solvents, accordingly, improves the shelf stability of polymeric compositions containing the neoalkoxy compounds. Rather than being useful for just minutes after blending with the resin, stability can now be extended for weeks. Actually, this is of substantial advantage in using the organo-titanates or organo-zirconates of the invention as coupling agents, rather than the conventional primary, secondary and tertiary alkoxy-type.

The reaction product of the neoalkoxy compounds and fillers are a further embodiment of the instant invention. Generally speaking at least 0.01 part, preferably from 0.1 to 5 parts by weight of the neoalkoxy compound are used to treat each 100 parts of filler. Most preferable is the reaction of from 0.2 to 2 parts per 100 parts of filler.

A wide variety of fillers may be treated; these include both organic and inorganic material. These materials may be particulate or fibrous and of varied shape or size, so long as the surfaces are reactive with the hydrolyzable groups of the organotitanium compound. Examples of inorganic reinforcing materials include metals, clay, carbon black, calcium carbonate, barium sulfate, silica, mica, glass and asbestos. Reactive inorganic materials include the metal oxides of zinc, magnesium, lead, and calcium and aluminum, iron filings and turnings, and sulfur. Examples of inorganic pigments include titanium dioxide, iron dioxides, zinc chromate, ultramarine blues. Organic materials include carbon black, carbon fibers, nylon fibers, polytetrafluoroethylene, cellulosics and organic pigments. As a practical matter, the particle size of the inorganic materials should not be greater than 1 mm, preferably from 0.1 micron to 500 micron.

It is imperative that the neoalkoxy compound be properly admixed with the inorganic material to permit the surface of the latter to react sufficiently. The optimum amount of the neoalkoxy compound to be used is dependent on the effect to be achieved, the available surface area of and the bonded water in the inorganic material.

Reaction is facilitated by admixing under the proper conditions. Optimum results depend on the properties of the alkoxy compound, namely, whether it is liquid or solid, and its decomposition and flash points. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate or zirconate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic metalate. Mixing is performed under conditions at which the organic metalate is in the liquid phase, at temperatures below the decomposition temperature. While it is desirable that the bulk of the hydrolyzable groups be reacted in this step, this is not essential where the materials are later admixed with a polymer, since the substantial completion of the reaction may take place in this latter mixing step.

Polymer processing, e.g., high shear mixing, is generally performed at a temperature well above the second order transition temperature of the polymer, desirably at a temperature where the polymer will have a low melt viscosity. For example, low density polyethylene is best processed at a temperature range of 170° to 230° C.; high density polyethylene from 200° to 245° C.; polystyrene from 230° to 260° C.; polypropylene from 230° to 290° C.; thermoplastic polyesters from 260° to 280° C.; polyamides from 260° to 320° C. and polycarbonates from 230° to 255° C. Temperatures for mixing other polymers are known to those skilled in the art and may be determined by reference to existing literature. A variety of mixing equipment may be used, e.g., two-roll mills, Banbury mixers, double concentric screws, counter or co-rotating twin screws and ZSK type of Werner and Pfaulder and Busse mixers.

When the organic metalate and the inorganic materials are dry-blended, thorough mixing and/or reaction is not readily achieved and the reaction may be substantially completed when the treated filler is admixed with the polymer. In this latter step, the organic metalate may also react with the polymeric material if one or more of the A groups is reactive with the polymer.

The treated filler may be incorporated in any of the conventional polymeric materials, whether thermoplastic or thermosetting, whether rubber or plastic. The amount of filler depends on the particular polymeric material, the filler and property requirements of the finished product. Broadly, from 10 to 500 parts of filler may be used per 100 parts of polymer, preferably from 20 to 250 parts. The optimum amount may be readily determined by one skilled in the art with the assistance of the following dosage table:

of each of the three components separately in a single operation. In the case of the prior art organo-titanate, where the blending of the polymer and filler required high- temperature, high-shear mixing, the addition of the three components at once would have resulted in the decomposition of the hydrolyzable group and the destruction of the coupling effect.

In order to further illustrate the subject invention, the following examples are provided. Examples 1 through 3 show the preparation of various neoalkoxy compounds of the invention. Example 4 shows the relative solvolytic stability. The balance of the examples are directed towards the use of the neoalkoxy compounds in resins, showing both filled and unfilled resin systems:

EXAMPLE 1

Titanium IV 2,2-Dimethyl Propanolato, Tris(Dioctyl)Phosphato-O

To a glass vessel equipped with a mechanical agitator, external heating and cooling, vapor condensation means, a distillate trap and off-gas scrubber was added

| Substrate-Class | Substrate-Type | Coupling Agent, wt. % based on Substrate |
|---|---|---|
| Polymers Organic/Inorganic | All types | 0.1–0.3 |
| Silicas Mineral | Sand, Quartz | 0.2 |
| | Novaculite | 0.3 |
| | Diatomaceous Earth | 0.6 |
| Synthetics | Precipitated Silica (Reinf.) | 0.6 |
| | Fumed Colloidal Silica | 0.8 |
| | Silica Aerogel | 0.8 |
| Silicates Mineral | Soft, Hard, Calcined Clay | 0.3 |
| | Mica, Talc | 0.3 |
| | Wollastonite, Perlite, Asbestos | 0.4 |
| Synthetics | Calcium Silicate | 0.6 |
| | Aluminum Silicate | 0.4 |
| Calcium Carbonate | Calcite, Dolomite | 0.2–0.5 |
| | Precipitated | 0.5 |
| Metals Plate | All Metals | 0.2–0.5 |
| Powder | All Metals | 0.2–0.4 |
| Oxides | Iron, Zinc, Lead, Chromium, Zirconium, Ti, Al, Mg, etc. | 0.2–0.4 |
| Peroxides | Lead Zinc | 0.3–0.5 |
| Hydrates | Aluminum, etc. | 0.2–0.4 |
| Acetates, Hydroxides | All Types | 0.2–0.4 |
| Sulfates, Nitrates | All Types | 0.2–0.4 |
| Sulfides | Zn, etc. | 0.2–0.4 |
| Borates | Ba, Zn | 0.1–0.5 |
| Carbon Black | Pigment, Reinf., Conductive | 0.5–2.0 |
| Fibers | Fiberglass | 0.2–0.3 |
| | Aramide (Kevlar) | 0.2–0.3 |
| | Graphite | 0.1–0.8 |
| | Polybenzimidazole | 0.2–0.3 |
| | Potassium Titanate | 0.2–0.4 |
| | PAN | 0.1–0.3 |
| | Carbon (PAN based) | 0.2–1.0 |
| Cellulosics | Wood Flour | 0.5–2.0 |
| Sulfur | Vulcanization Grade | 0.3–0.5 |
| Pigments Chromates | Lead Chromate | 0.2–0.3 |
| | Molybdate Orange | 0.2–0.3 |
| | Chromate Green | 0.2–0.3 |
| Ferriferrocyanide | Iron Blue | 0.3–0.5 |
| Monoazo | Tol. Red, etc. | 0.3–0.5 |
| Lithol | Lithol Red | 0.3–0.5 |
| Rubine | Rubine Red | 0.3–0.5 |
| Phthalo | Blue, Green | 0.4–0.6 |
| Oxides | $TiO_2$ | 0.4–0.6 |
| | Iron | 0.2–0.4 |

As mentioned previously, because of the outstanding heat stability of the neoalkoxy compounds, it is unnecessary to first treat the filler in order to obtain the benefits of the neoalkoxy compounds as coupling agents, since their stability at high temperatures permits the blending one mole of 2,2-dimethylpropanol and three moles of dioctyl hydrogen phosphate as well as two liters of mixed isomer xylene. The reactor was flushed with nitrogen and maintained under a slow nitrogen purge during the addition of one mole of titanium tetrachloride over a period of two hours. External heating and cooling was supplied, as necessary, to maintain the operating temperature in the range of 45°–60° C. After the addition of the titanium tetrachloride, nitrogen purge was slightly accelerated for an additional two hours followed by evaporation of the reaction mixture in vacuo to produce a bottoms fraction boiling above 150° C. Elemental analysis of the moderately viscous red-brown residual oil was consistent with its formulation as $C_5H_{11}OTi[OP(O)(OC_8H_{17})_2]_3$. The off-gas scrubber contents were analyzed to show that approximately 4 moles of hydrogen chloride had been captured in the caustic scrubbing solution. Subsequent high pressure liquid chromatography (HLPC) analysis of a portion of bottoms product was used to determine product yield employing a Fourier transform infrared detector system (FTIR) for quantification of effluent assay. Results for the above preparation and for those producing analogous products by similar means from titanium tetrachloride together with the product yields are shown in Table 1. The Code in the lefthand column of the table is to designate these products in subsequent examples:

| Code | Calculated for C/H/Ti | Found for C/H/Ti |
|---|---|---|
| A | $C_{49}H_{113}O_{13}P_3Ti$-60.6/11.1/4.58 | 60.4/10.9/4.63 |
| B | $C_{23}H_{26}O_4Ti$-66.7/6.28/11.6 | 66.8/6.19/11.7 |
| C | $C_{43}H_{78}O_9Ti$-65.6/9.92/6.11 | 65.7/9.98/6.21 |
| G | $C_{32}H_{66}O_{23}P_6Ti$-36.5/6.27/4.56 | 36.7/6.18/4.51 |

EXAMPLE 2

Preparation of Titanium IV 2-Methyl,2-Phenylbutanolato,Bis(Dibutyl)Phosphato-O,(Dioctylphenyl)Pyrophosphato-O A reactor such as that described in Example 1 was charged with one mole of titanium IV tetrabutoxide. Temperature was adjusted to 50° C. and maintained between 50° C. and 70° C. by external heating and cooling and reactor pressure held at 10 mm of Hg. during the addition, sequentially, of one mole of 2-methyl-2-phenylbutanol (20 minutes), two moles of dibutyl phosphate (1 hour, 5 minutes), and one mole of dioctylphenyl pyrophosphate (1 hour, 45 minutes).

During the addition, the distillate was collected and determined by gas liquid chromatography to be essentially pure butanol totaling 3.84 moles. The residual reaction product was analyzed by HLPC/FTIR as described in Example 1. Results of this experiment and of several products made by analogous means are shown in Table 2 on a per mole of titanium tetralkoxide basis:

TABLE 1

| Code | Raw Materials | Product Structure | Yield (mole %) via HLPC/FT-IR |
|---|---|---|---|
| A | $(CH_3)_3CCH_2OH$<br>$3HOP(O)(OC_8H_{17})_2$ | $(CH_3)_3CCH_2OTi[OP(O)(OC_8H_{17})_2]_3$ | 87 |
| B | $(CH_3)_3CCH_2OH$<br>$3HOC_6H_5$ | $(CH_3)_3CCH_2OTi(OC_6H_5)_3$ | 92 |
| C | $(CH_2=CHCH_2OCH_2)_2(C_2H_5)CCH_2OH$<br>$3HOC(O)neo-C_9H_{19}$ | $(CH_2=CHCH_2OCH_2)_2(C_2H_5)CCH_2OTi$<br>$[OC(O)neo-C_9H_{19}]_3$ | 90 |
| D | $(C_6H_5)(CH_3OCH_2)(CH_3)CCH_2OH$<br>$3HOS(O)_2C_6H_4C_{12}H_{25}$ | $(C_6H_5)(CH_3OCH_2)(CH_3)CCH_2OTi$<br>$(OS(O)_2C_6H_4C_{12}H_{25})_3$ | 87 |
| F | $(C_{10}H_7-1-O)(C_2H_5)_2CCH_2OH$<br>$3HSC_6H_4-1-OCH_3$ | $(C_{10}H_7-1-O)(C_2H_5)_2CCH_2OTi$<br>$(SC_6H_4-1-OCH_3)_3$ | 92 |
| G | $(CH_3O)(C_6H_5)(iso-C_8H_{17})CCH_2OH$<br>$3(HO)_2(C_4H_9O)CH_3O)P_2O_3$ | $(CH_3O)(C_6H_5)iso-C_8H_{17})CCH_2OTi$<br>$[OP(O)(OH)OP(O)(OC_4H_9)(OCH_3)]_3$ | 84 |

The empirical formula, the calculated and analysed values for certain of the above products are as follows:

TABLE 2

| Code | Raw Materials | Product Structure | Yield (mole %) via HLPC/FT-IR |
|---|---|---|---|
| H | $(CH_3)(C_6H_5)(C_2H_5)CCH_2OH$<br>$2HOP(O)(OC_4H_9)_2$<br>$(HO)_2(C_8H_{17}C_6H_4O)_2P_2O_3$ | $(CH_3)(C_6H_5)(C_2H_5)CCH_2OTi$<br>$[OP(O)(OC_4H_9)_2]_2$<br>$[OP(O)(OH)OP(O)(OC_6H_{17}C_8H_{17})_2]$ | 71 |
| J | $(CH_2=CHCH_2OCH_2)_2(C_2H_5)(CCH_2OH$<br>$HOC(O)iso-C_{17}H_{35}$<br>$2HOS(O)_2C_6H_4C_{12}H_{25}$ | $(CH_2=CHCH_2OCH_2)_2(C_2H_5)CCH_2OTi$<br>$[OC(O)iso-C_{17}H_{35}]$<br>$[OS(O_2)C_6H_4C_{12}H_{25}]_2$ | 62 |
| B | $(CH_3)_3CCH_2OH$<br>$3HOC_6H_5$ | $(CH_3)_3CCH_2OTi(OC_6H_5)_3$ | 96 |
| K | $(CH_2=CHCH_2OCH_2)_2(C_2H_5)C$<br>$CH_2OH$<br>$3(HO)_2(C_8H_{17}O)_2P_2O_3$ | $(CH_2=CHCH_2OCH_2)_2(C_2H_5)$<br>$CCH_2OTi[OP(O)(OH)OP(O)(OC_8H_{17})_2]_3$ | 85 |
| L | $(CH_3O)(C_4H_9)(C_6H_5)(CCH_2OH$<br>$HOC(O)CH_3$<br>$2HSC_6H_4C_8H_{17}$ | $(CH_3O)(C_4H_9)(C_6H_5)CCH_2OTi[OC(O)CH_3]$<br>$[SC_6H_4C_8H_{17}]_2$ | 75 |
| M | $(CH_2=CHCH_2OCH_2)(C_8H_{17}OCH_2)$<br>$(C_2H_5)CCH_2OH$<br>$3(HO)_2(C_8H_{17}O)_2P_2O_3$ | $(CH_2=CHCH_2OCH_2)(C_8H_{17}OCH_2)(C_2H_5)$<br>$CCH_2OTi[OP(O)(OH)OP(O)(OC_8H_{17})_2]_3$ | 63 |
| N | $(CH_2=CHCH_2OCH_2)_2(C_2H_5)$<br>$CCH_2OH$<br>$3HOP(O)(OC_8H_{17})_2$ | $(CH_2=CHCH_2OCH_2)_2(C_2H_5)CCH_2OTi$<br>$[OP(O)(OC_8H_{17})_2]_3$ | 74 |
| P | $neo-C_{10}H_{21}OH$<br>$2\ HOS(O)_2C_{10}H_6-3-CH_3$ | $neo-C_{10}H_{21}OTi[OS(O)_2C_{10}H_6-3-CH_3]_2$<br>$[OS(O)_2C_6H_4-p-C_2H_5$ | 61 |

TABLE 2-continued

| Code | Raw Materials | Product Structure | Yield (mole %) via HLPC/FT-IR |
|------|---------------|-------------------|-------------------------------|
|      | $HOS(O)_2C_6H_5-p-C_2H_5$ |  |  |

The empirical formula, the calculated and analysed values for certain of the above compounds are as follows:

| Code | Calculated for C/H/Ti | Found for C/H/Ti |
|------|------------------------|------------------|
| B | $C_{23}H_{26}O_4Ti$-60.6/11.1/4.58 | 60.7/11.3/4.62 |

HLPC effluents as described in Example 1 (after toluene evaporation in vacuo) indicated that a 73 mole % yield of titanium IV (2-allyloxymethyl, 2-n-propanolatomethyl-1)butanolato, tri(dioctyl)pyrophosphato-O was obtained. Similarly, isostearate, phosphate and amino analogs were prepared as shown in Table 3.

TABLE 3

| Code | Raw Materials | Product Structure | Yield (mole %) via HLPC/FT-IR |
|------|---------------|-------------------|-------------------------------|
| Q | $[(C_2H_5)(C_3H_7OCH_2)(CH=CHCH_2OCH_2)CCH_2O]_4Ti$ $3Ti[OP(O)(OH)OP(O)(OC_8H_{17})_2]_4$ $[OP(O)(OC_8H_{17})OP(O)(OH)(OC_8H_{17})]$ | $(C_2H_5)(C_3H_7OCH_2)(CH_2=CHCH_2OCH_2)CCH_2OTi[OP(O)(OH)OP(O)(OC_8H_{17})_2]_3$ | 73 |
| R | $[(C_2H_5)(C_3H_7OCH_2)(CH_2=CHCH_2OCH_2)CCH_2O]_4Ti$ $3Ti[OC(O)iso\text{-}C_{17}H_{35}]_4$ | $(C_2H_5)(C_3H_7OCH_2)(CH_2CHCH_2OCH_2)CCH_2OTi[OC(O)iso\text{-}C_{17}H_{35}]_3$ | 79 |
| S | $[(C_2H_5)(C_3H_7OCH_2)(CH_2=CHCH_2OCH_2)CCH_2O]_4Ti$ $3Ti[OP(O)(OC_8H_{17})_2]_4$ | $(C_2H_5)(C_3H_7OCH_2)(CH_2=CHCH_2OCH_2)CCH_2OTi[OP(O)(OC_8H_{17})_2]_3$ | 83 |
| T | $[(C_6H_5CH_2)_2(C_6H_5)CCH_2O]_4Ti$ $3Ti[OP(O)(CH_3C_6H_4O)_2]_4$ | $(C_6H_5CH_2)_2(C_6H_5)CCH_2OTi$ $[OP(O)(OC_6H_4CH_3)_2]_3$ | 71 |
| U | $[(CH_2=CHCH_2OCH_2)_2(C_2H_5)CCH_2O]_4Ti$ $3Ti[OC_2H_4NHC_2H_4NH_2]_4$ | $(CH_2=CHCH_2OCH_2)_2(C_2H_5)CCH_2OTi$ $[OC_2H_4NHC_2H_4NH_2]_3$ | 70 |
| V | $[(CH_2=CHCH_2OCH_2)_2(C_2H_5)CCH_2]_4Ti$ $3Ti[OS(O)_2C_6H_4C_{12}H_{25}]_4$ | $(CH_2=CHCH_2OCH_2)_2(C_2H_5)CCH_2OTi$ $(OS(O)_2C_6H_4C_{12}H_{25})_3$ |  |
| W | $[(CH_2=CHCH_2OCH_2)_2(C_2H_5)CCH_2]_4Ti$ $3Ti[OC_6H_4NH_2]_4$ | $(CH_2=CHCH_2OCH_2)_2(C_2H_5)CCH_2OTi$ $(OC_6H_4NH_2)_3$ |  |
| Z1 | $[(CH_2=CHCH_2OCH_2)_2(C_2H_5)CCH_2]_4Zr$ $3Zr[OC(O)C_9H_{19}]_4$ | $(CH_2=CHCH_2OCH_2)_2(C_2H_5)CCH_2OZr$ $(OC(O)C_9H_{19})_3$ |  |
| Z2 | $[(CH_2=CHCH_2OCH_2)_2(C_2H_5)CCH_2]_4Zr$ $3Zr[OC_6H_4NH_2]_4$ | $(CH_2=CHCH_2OCH_2)_2(C_2H_5)CCH_2OZr$ $(OC_6H_4NH_2)_3$ |  |
| Z3 | $[(CH_2=CHCH_2OCH_2)_2(C_2H_5)CCH_2]_4Zr$ $3Zr[OP(OC_8H_{17})_2]_4$ | $(CH_2=CHCH_2OCH_2)_2(C_2H_5)CCH_2OZr$ $(OP(OC_8H_{17})_2)_3$ |  |
| Z4 | $[(CH_2=CHCH_2OCH_2)_2(C_2H_5)CCH_2]_4Zr$ $3Zr[(OP(O)(OH)OP(O)(OC_8H_{17})_2]_4$ | $(CH_2=CHCH_2OCH_2)_2(C_2H_5)CCH_2OZr$ $(OP(O)(OH)OP(O)(OC_8H_{17})_2)_3$ |  |
| Z5 | $[(CH_2=CHCH_2OCH_2)_2(C_2H_5)CCH_2]_4Zr$ $3Zr[OC_2H_4NHC_2H_4NH_2]_4$ | $(CH_2=CHCH_2OCH_2)_2(C_2H_5)CCH_2OZr$ $(OC_2H_4NHC_2H_4NH_2)_3$ |  |
| Z6 | $[(CH_2=CHCH_2OCH_2)_2(C_2H_5)CCH_2]_4Zr$ $3Zr[OC_6H_4NH_2]_4$ | $(CH_2=CHCH_2OCH_2)_2(C_2H_5)CCH_2OZr$ $(OC_6H_4NH_2)_3$ |  |

| K | $C_{44}H_{126}O_{24}P_6Ti$-41.5/9.91/3.77 | 41.6/9.82/3.75 |
|---|---|---|
| L | $C_{43}H_{64}O_4S_2Ti$-68.3/8.47/6.35 | 68.3/8.39/6.41 |
| M | $C_{49}H_{138}O_{23}P_6Ti$-44.3/10.4/3.61 | 44.1/10.3/3.56 |
| N | $C_{44}H_{123}O_{14}P_3Ti$-60.9/14.2/5.54 | 60.6/14.1/5.58 |
| P | $C_{40}H_{48}O_{10}S_3Ti$-57.7/5.77/5.77 | 57.6/5.84/5.69 |

EXAMPLE 3

Production of Neoalkoxy Titanium VI Salts From Titanium IV Salts and Titanium Tetrakis Neoalkoxylates One mole of titanium IV tetrakis(2-allyloxymethyl, 2-propanolato methyl-1-)butanolato was added over a period of two hours to 3 moles of titanium IV tetrakis(-dioctyl)pyrophosphato-O contained in 1 liter of toluene. The reaction mixture was agitated and maintained at 75±5° C. during the addition and for 24 hours after by external heating and cooling. FTIR analysis of The calculated and analysed values for certain of the above compounds are as follows:

| Code | Calculated for C/H/Ti | Found for C/H/Ti |
|------|-----------------------|------------------|
| Q | $C_{44}H_{128}O_{24}P_6Ti$-41.4/10.0/3.77 | 41.5/10.3/3.84 |
| R | $C_{66}H_{128}O_9Ti$-73.2/11.8/4.44 | 73.0/11.6/4.38 |
| S | $C_{44}H_{125}O_{14}P_3Ti$-60.8/14.4/5.52 | 60.6/14.7/5.59 |
| U | $C_{24}H_{54}O_6N_6Ti$-50.5/9.47/8.42 | 50.3/9.59/8.56 |

Examples Nos. 4 through 30 demonstrate the surprising superiority of the products of the instant invention as compared to their heretofore known analogs. The following codes are used to designate analogs of the neoalkoxy titanates for comparative purposes:

| COMPOUND | CODE |
|---|---|
| i-$C_3H_7$OTi[OP(O)(O$C_8H_{17}$)$_2$]$_3$ | AA |
| n-$C_8H_{17}$OTi[OP(O)(O$C_8H_{17}$)$_2$]$_3$ | AB |
| (2-$C_2H_5$)$C_6H_{12}$OTi[OP(O)(O$C_8H_{17}$)$_2$]$_3$ | AC |
| i-$C_3H_7$OTi[OC(O)neo-$C_9H_{19}$]$_3$ | AD |
| $C_6H_5CH_2$OTi[OC(O)neo-$C_9H_{19}$]$_3$ | AE |
| ($CH_3OC_2H_4O$)$_3$SiCH=$CH_2$ | AF |
| i-$C_3H_7$OTi[OC(O)iso-$C_{17}H_{35}$]$_3$ | AG |
| ($CH_3OC_2H_4O$)$_3$Si$CH_3$ | AH |
| $C_3H_7$OTi[OP(O)(OH)OP(O)(O$C_8H_{17}$)$_2$]$_3$ | AJ |
| $C_8H_{17}$OTi[OP(O)(OH)OP(O)(O$C_8H_{17}$)$_2$]$_3$ | AK |
| i-$C_3H_7$OTi[OS(O)$_2C_6H_4C_{12}H_{25}$]$_3$ | AL |
| $C_6H_5CH_2$OTi[OS(O)$_2C_6H_3(CH_3)_2$]$_3$ | AM |
| ($CH_3O$)$_3$Si$C_3H_6$SH | AN |
| (i-$C_3H_7O$)Ti[O$C_6H_4C(CH_3)_2C_6H_5$]$_3$ | AO |
| ($C_2H_5O$)$_3$Si$C_3H_6NH_2$ | AP |
| (i-$C_3H_7O$)Ti[O$C_2H_4NHC_2H_4NH_2$]$_3$ | AQ |
| ($CH_3O$)$_3$Si$C_6H_5$ | AR |
| ($CH_3O$)$_3$Si$C_3H_6NHC_2H_4NH_2$ | AS |
| ($C_8H_{17}$)Ti[O$C_6H_4C(CH_3)_2C_6H_5$]$_3$ | AT |
| (i-$C_3H_7O$)Ti[OC(O)$C_7H_{15}$]$_3$ | AU |
| O($CH_3O$)Si$C_3H_6OCH_2$CH=$CH_2$ | AV |

EXAMPLE 4

Evaluation of the Relative Solvolytic Stabilities

Five weight percent solutions of the indicated species were maintained at 25±2° C. and the time required for 50% of the solute to disappear was measured by FTIR. Results given in Table 4 clearly establish the superiority of the Titanium IV salts of the instant invention as compared to heretobefore known titanate and silicone compounds with respect to solvolysis resistance.

TABLE 4

SOLVOLYTIC STABILITY OF TITANIUM IV SALTS

| Product Designation | Solvent | Product Half Life |
|---|---|---|
| A | n-$C_4H_9$OH | 48 hr. |
| AA | " | 0.1 hr. |
| C | 5% $H_2O$, 95% $C_2H_5$C(O)$CH_3$ | 7 hr. |
| J | " | 4 hr. |
| AG | " | 1 min. |
| AH | " | 0.2 hr. |
| Q | $C_6H_5$OH | 48 hr. |
| K | " | 48 hr. |
| H | " | 48 hr. |
| AJ | " | 0.1 hr. |
| AN | " | 2 hr. |

EXAMPLE 5

Clay Filled Diallyl Phthalate Resin

Molding compound (Cosmic Resin D-45) containing 50% clay filler was tumble blended with 0.3% by weight of additive and compression molded at 170° C. to form test specimens using RF preheat. Results are given in Table 5.

TABLE 5

| Additive | Strength MPa ASTM D638 | Strength MPa ASTM D790 | Modulus GPa ASTM D790 | Notched Izod KJ/M ASTM D256 | Equilibrium Water Absorption ASTM D570 |
|---|---|---|---|---|---|
| None | 37 | 61 | 8.3 | 0.2 | 0.55 |
| AF | 38 | 68 | 8.9 | 0.1 | 0.48 |
| AO | 42 | 58 | 8.1 | 0.3 | 0.42 |
| B | 48 | 68 | 8.7 | 0.3 | 0.44 |
| N | 46 | 68 | 8.1 | 0.3 | 0.36 |
| U | 51 | 67 | 9.9 | 0.4 | 0.27 |

Note that the products of this invention (B, N, U) were generally more effective than the prior art additives in enhancing the tensile, flexural and impact strengths as well as hydrophobicity of the tested commercial mineral filled diallylphthalate based resin.

EXAMPLE 6

Carbon Black Filled Thermoplastic Polyurethane

Each additive shown in the table below was independently metered into the throat of a compounding extruder at a level of 0.25 wt. % based on preblended, meter-fed mix containing: 25.00 wt. % Vulcan 6 Carbon Black (Cabot Corp.) and 74.75 wt. % Pelethane CPR2102-90AE thermoplastic polyurethane (Upjohn) and subsequently compounded at 230°–240° C. followed by injection molding of test specimens at 235° C. Results are given in Table 6:

TABLE 6

| Additive | Tensile MPa ASTM D638 | % Elongation ASTM D638 | Flexural Modulus GPa ASTM D790 | Volume Resistivity Ohm-cm ASTM D257 |
|---|---|---|---|---|
| None | 27 | 45 | 1.8 | 1 × $10^4$ |
| U | 52 | 420 | 3.1 | 2 × $10^1$ |
| Q | 41 | 135 | 2.4 | 3 × $10^2$ |
| J | 40 | 115 | 2.6 | 4 × $10^2$ |
| K | 42 | 85 | 2.3 | 5 × $10^3$ |
| S | 36 | 70 | 2.3 | 4 × $10^2$ |
| AP | 30 | 55 | 2.8 | 2 × $10^4$ |
| AQ | 29 | 64 | 2.4 | 8 × $10^3$ |

Note that in each and every instance, the products of the instant invention provide substantially greater tensile, elongation and conductivity enhancement as compared to the prior art.

EXAMPLE 7

Talc Filled Acrylonitrile-Butadiene Styrene Resin

The compounding process consisted of separate meter feed each of 40.0 wt. % talc (Mistron Vapor-Cyprus Mines), 59.8 wt. % ABS (Taitalc Chemical Co.) and 0.2 wt. % of a 65 wt. % active additive on a silica powder concentrate to the throat of a 28:1 WP ZSK extruder using a graduated 210° to 240° C. extrusion profile. Test specimens were injection molded at 230° C. The results are shown in Table 7:

TABLE 7

| Additive | Tensile Strength MPa ASTM D638 | % Elongation ASTM D638 | Flexural Strength MPa ASTM D790 | Flexural Modulus GPa ASTM D790 | Notched Izod KJ/M ASTM D256 |
|---|---|---|---|---|---|
| None | 37 | 25 | 70 | 2.5 | 0.2 |
| A | 42 | 35 | 78 | 2.4 | 0.4 |
| B | 41 | 38 | 82 | 2.9 | 0.3 |
| C | 39 | 34 | 80 | 2.5 | 0.4 |
| K | 42 | 36 | 76 | 2.5 | 0.5 |
| AA | 37 | 28 | 70 | 2.2 | 0.3 |
| AR | 38 | 26 | 70 | 2.4 | 0.2 |

Note that the products of the instant invention provided superior tensile, elongation and impact property enhancement as compared with the prior art.

EXAMPLE 8

Thermoset Polyurethane

Liquid additive (0.2 wt. %) was added to 60% mica (Suzerite-Martin Marietta Corp.) filled resin (Uralite 3167—Hexcel) and admixed thoroughly by means of a static mixer and gear pump just prior to ambient casting. The resultant sheets were die cut for testing. The results are shown in Table 8:

TABLE 8

| Additive | Tensile Strength MPa ASTM D638 | % Elongation ASTM D638 | Flexural Modulus GPa ASTM D790 | Compression Strength MPa ASTM D695 | Notched Izod KJ/M ASTM D256 |
|---|---|---|---|---|---|
| None | 27 | 25 | 4.7 | 55 | 0.3 |
| U | 39 | 370 | 6.0 | 72 | 0.9 |
| D | 35 | 280 | 5.1 | 63 | 0.6 |
| M | 36 | 310 | 5.0 | 64 | 0.6 |
| S | 34 | 260 | 4.7 | 68 | 0.7 |
| C | 36 | 240 | 5.0 | 57 | 0.8 |
| AS | 31 | 120 | 4.8 | 70 | 0.3 |
| AG | 30 | 280 | 4.6 | 55 | 0.8 |

Note that in the mica filled thermoset urethane casting resin system, the products of the instant invention provided a better overall set of physical properties than did prior art analogs.

EXAMPLE 9

Calcium Carbonate Filled Thermoset Polyester

The additives indicated on Table 10 were added (as 65% active additive dryblends on silica) directly to the compression-melt pot containing 30 wt. % thermoset polyester (Reichhold #3003) and 70% $CaCO_3$ at levels of 0.3 wt. % dryblend prior to melt generation@180° C. The results are tabulated in the Table:

TABLE 9

| Additive | Tensile MPa ASTM D638 | % Elongation ASTM D638 | Flexural Modulus GPa ASTM D790 | Notched Izod KJ/M ASTM D256 | Melt Flow Index ASTM D1238 |
|---|---|---|---|---|---|
| None | 66 | 0.2 | 1.3 | 0.04 | 3.0 |
| B | 78 | 0.9 | 1.9 | 0.07 | 5.7 |
| F | 75 | 0.6 | 1.8 | 0.09 | 5.2 |
| J | 75 | 0.7 | 1.9 | 0.10 | 5.4 |
| K | 77 | 0.7 | 1.7 | 0.10 | 5.1 |
| S | 72 | 0.4 | 1.5 | 0.05 | 4.3 |
| AG | 65 | 0.5 | 1.3 | 0.07 | 4.4 |
| AB | 64 | 0.5 | 1.4 | 0.07 | 4.5 |
| AF | 68 | 0.2 | 1.5 | 0.03 | 3.3 |
| AP | 70 | 0.2 | 1.6 | 0.04 | 3.2 |

The data on Table 9 clearly establish the superiority of the products of the instant invention as compared to prior art with respect to enhancement of rheology and physical properties in mineral filled compression molded thermoset polyester.

EXAMPLE 10

Filled and Unfilled Polybutylene Terephthalate

Formulations were prepared by batch tumble blending of the appropriate proportions of PBT (Gafite 1600A, GAF Corp.) and mica (Suzerite-Martin Marietta) together with 0.3 wt. % of additive by weight of mica content in a doublt cone type blender prior to extrusion in a 24:1 NRM two stage vented extruder at approximately 250±10° C. with a virtually flat temperature profile. Test samples were injection molded at 240° C. and annealed for 48 hrs. at 100° C. prior to test. Results are given in Table 10:

TABLE 10

| Additive | % Mica | Tensile MPa ASTM D638 | Flexural Strength at Yield MPa ASTM D638 | Flexural Modulus GPa ASTM D790 | Notched Izod KJ/M ASTM D256 | % Elongation ASTM D638 |
|---|---|---|---|---|---|---|
| None | None | 69 | 83 | 2.3 | 1.0 | 260 |
| C | " | 74 | 91 | 2.5 | 1.5 | 360 |
| J | " | 71 | 87 | 2.4 | 1.3 | 340 |
| N | " | 78 | 89 | 2.2 | 1.4 | 350 |
| T | " | 74 | 83 | 2.4 | 1.3 | 340 |
| AA | " | 67 | 80 | 1.6 | 1.4 | 250 |
| AT | " | 65 | 77 | 1.5 | 1.6 | 340 |
| AR | " | 69 | 81 | 2.0 | 1.1 | 240 |
| None | 30 | 81 | 121 | 8.2 | 0.1 | 3 |
| C | 30 | 84 | 127 | 9.1 | 0.6 | 16 |
| J | 30 | 86 | 129 | 9.3 | 0.7 | 35 |
| N | 30 | 84 | 126 | 9.0 | 0.5 | 20 |
| T | 30 | 89 | 124 | 8.6 | 0.5 | 30 |
| AA | 30 | 78 | 117 | 7.8 | 0.2 | 4 |
| AT | 30 | 80 | 115 | 7.6 | 0.2 | 5 |
| AR | 30 | 79 | 116 | 7.9 | 0.2 | 3 |
| None | 50 | 82 | 124 | 10.2 | 0.07 | 2 |
| C | 50 | 85 | 129 | 10.8 | 0.25 | 11 |
| J | 50 | 84 | 147 | 10.7 | 0.40 | 8 |
| N | 50 | 84 | 147 | 10.9 | 0.40 | 6 |
| T | 50 | 86 | 148 | 10.0 | 0.30 | 7 |
| AA | 50 | 80 | 135 | 9.9 | 0.10 | 2.5 |
| AT | 50 | 81 | 137 | 9.9 | 0.10 | 2.5 |
| AR | 50 | 80 | 133 | 9.6 | 0.10 | 1.5 |

Note that in each and every instance, the products of the instant invention had superior overall properties as compared to those of the prior art.

EXAMPLE 11

Precompounded Mineral Filled Polybutylene Terphthalate

The indicated additives were high shear blended with precompounded 30% mineral filled polyester (Valox 746, General Electric) pellets at 0.2 wt. % additive based on total weight, and the resulting composites injection molded at 250° C. to produce test specimens. Results are tabulated in Table 11.

TABLE 11

| Additive | Tensile MPa ASTM D638 | Flexural Strength at Yield MPa ASTM D790 | Flexural Modulus GPa ASTM D790 | Notched Izod KJ/M ASTM D256 | % Elongation ASTM D638 | UL 94 Rating @ 0.25" |
|---|---|---|---|---|---|---|
| None | 62 | 220 | 4.5 | 0.05 | 15 | HB2 |
| A | 68 | 135 | 4.2 | 0.25 | 40 | V2 |
| G | 64 | 127 | 4.5 | 0.20 | 70 | V2 |
| K | 67 | 134 | 4.6 | 0.30 | 65 | V1 |
| M | 67 | 131 | 4.4 | 0.10 | 55 | V1 |
| AA | 61 | 108 | 4.2 | 0.05 | 20 | HB2 |
| AJ | 61 | 105 | 4.0 | 0.04 | 15 | HB2 |
| AP | 62 | 96 | 4.0 | 0.04 | 12 | HB2 |

This data shows the superiority of the additives of the instant invention as compared to prior art for the purposes of enhancing the physical properties and flame retardance of injection molded mineral filled polybutylene terphthalate.

EXAMPLE 12

Polyacrylonitrile Based Carbon Fiber Filled Polyether Ether Ketone Resin

Thirty percent filled formulations were prepared by downstream carbon fiber (Union Carbide) loading of molten PEEK (ICI) in a twin screw extruder at approximately 400° C. Test specimens were injection molded at 380° C. Additives were throat fed at 0.2 wt. % on resin as 65% concentrates on silica powder. Results are given in Table 12:

TABLE 12

| Additive | Tensile MPa ASTM D638 | % Elongation ASTM D638 | Flexural Modulus GPa ASTM D790 | Equilibrium Water Absorption ASTM D570 | Notched Izod KJ/M ASTM D256 | Resistivity Ohm-cm ASTM D257 |
|---|---|---|---|---|---|---|
| None | 215 | 3 | 15.5 | 0.10 | 0.06 | $1.4 \times 10^5$ |
| J | 255 | 90 | 15.0 | 0.06 | 0.35 | $8 \times 10^2$ |
| M | 205 | 75 | 17.0 | 0.05 | 0.45 | $3 \times 10^1$ |
| N | 280 | 105 | 13.5 | 0.05 | 0.30 | $8 \times 10^1$ |
| C | 220 | 60 | 15.0 | 0.08 | 0.20 | $9 \times 10^2$ |
| K | 240 | 55 | 16.0 | 0.09 | 0.25 | $1 \times 10^3$ |
| AL | 190 | 8 | 15.0 | 0.15 | 0.06 | $1 \times 10^5$ |
| AA | 160 | 12 | 15.0 | 0.10 | 0.05 | $7 \times 10^4$ |

TABLE 12-continued

| Additive | Tensile MPa ASTM D638 | % Elongation ASTM D638 | Flexural Modulus GPa ASTM D790 | Equilibrium Water Absorption ASTM D570 | Notched Izod KJ/M ASTM D256 | Resistivity Ohm-cm ASTM D257 |
|---|---|---|---|---|---|---|
| AF | 180 | 3 | 15.0 | 0.10 | 0.04 | $2 \times 10^5$ |
| AV | 180 | 3 | 14.0 | 0.10 | 0.05 | $2 \times 10^5$ |

Note that the additives of the instant invention improved the elongation, water absorption inhibition, impact resistance and electrical conductivity while those properties were generally negatively effected by inclusion of prior art analog additives.

EXAMPLE 13

Filled Polypropylene

Polypropylene (Elex PTL 220, Solvey) filled with various types of particulate the amounts shown in Tables 13A to 13D and 0.3 wt. % of additives. These were extruded at temperatures of 230°–260° C. and test samples were compression molded at 250° C. The results are given in Tables 13A to 13D.

TABLE 13A

40% CALCIUM CARBONATE FILLED

| Additive | Tensile MPa ASTM D638 | % Elongation ASTM D638 | Flexural Strength at Yield MPa ASTM D790 | Flexural Modulus GPa ASTM D790 | Notched Izod KJ/M ASTM D256 |
|---|---|---|---|---|---|
| None | 23 | 45 | 45 | 2.5 | 0.03 |
| D | 28 | 110 | 70 | 2.8 | 0.07 |
| N | 26 | 125 | 67 | 3.2 | 0.10 |
| R | 23 | 90 | 55 | 3.0 | 0.15 |
| AG | 19 | 120 | 40 | 2.1 | 0.10 |
| AC | 19 | 130 | 37 | 2.2 | 0.10 |

Note the products of the instant invention do not sacrifice tensile and flexural properties in order to provide enhanced impact and elongation ones as do the prior art materials.

TABLE 13B

40% USP TALC FILLED

| Additive | Tensile MPa ASTM D638 | % Elongation ASTM D638 | Flexural Strength at Yield MPa ASTM D790 | Flexural Modulus GPa ASTM D790 | Notched Izod KJ/M ASTM D256 |
|---|---|---|---|---|---|
| None | 28 | 6 | 47 | 2.9 | 0.03 |
| C | 32 | 82 | 55 | 3.4 | 0.07 |
| D | 39 | 75 | 58 | 3.0 | 0.10 |
| N | 34 | 80 | 49 | 3.2 | 0.10 |
| R | 36 | 95 | 52 | 3.4 | 0.08 |
| AG | 22 | 80 | 41 | 2.6 | 0.06 |
| AB | 21 | 72 | 42 | 2.5 | 0.06 |

Note the products of the instant invention gave enhanced elongation, tensile properties and improved impact properties without the loss of flexural strength and modulus caused by prior art compounds.

TABLE 13C

40% MICA FILLED

| Additive | Tensile MPa ASTM D638 | % Elongation ASTM D638 | Flexural Strength at Yield MPa ASTM D790 | Flexural Modulus GPa ASTM D790 | Notched Izod KJ/M ASTM D256 |
|---|---|---|---|---|---|
| None | 41 | 6 | 62 | 4.0 | 0.03 |
| C | 46 | 55 | 70 | 4.6 | 0.08 |
| D | 47 | 38 | 67 | 4.2 | 0.07 |
| AC | 37 | 32 | 48 | 3.6 | 0.04 |
| AG | 35 | 25 | 55 | 3.7 | 0.05 |

Note the products of the instant invention gave enhanced elongation, tensile properties and improved impact properties without the loss of the flexural strength and modulus caused by prior art compounds.

TABLE 13D

25% CARBON POWDER FILLED

| Additive | Tensile MPa ASTM D638 | % Elongation ASTM D638 | Flexural Strength at Yield MPa ASTM D790 | Flexural Modulus GPa ASTM D790 | Notched Izod KJ/M ASTM D256 | Melt Flow Index ASDM D1238 | Conductivity |
|---|---|---|---|---|---|---|---|
| None | 29 | 20 | 39 | 1.4 | 0.1 | 0.05 | $2 \times 10^3$ |
| C | 32 | 45 | 46 | 1.8 | 0.3 | 0.25 | $3 \times 10^1$ |
| J | 33 | 52 | 43 | 1.5 | 0.4 | 0.20 | $2 \times 10^1$ |
| K | 30 | 57 | 44 | 1.7 | 0.4 | 0.20 | $8 \times 10^0$ |
| M | 34 | 49 | 52 | 2.0 | 0.3 | 0.30 | $1 \times 10^1$ |
| N | 35 | 37 | 41 | 1.6 | 0.4 | 0.20 | $1 \times 10^1$ |
| R | 30 | 36 | 46 | 1.7 | 0.4 | 0.15 | $2 \times 10^1$ |
| AG | 25 | 24 | 35 | 1.1 | 0.2 | 0.10 | $5 \times 10^2$ |
| AB | 23 | 26 | 37 | 1.0 | 0.2 | 0.10 | $1 \times 10^3$ |
| AA | 27 | 22 | 34 | 1.1 | 0.2 | 0.10 | $9 \times 10^2$ |
| AV | 21 | 17 | 31 | 1.1 | 0.1 | 0.05 | $3 \times 10^3$ |

The data in Table 13D clearly demonstrates the superiority of the products of the instant invention as compared to prior art analogs with respect to melt flow enhancement, conductivity and general physical property improvement when they are employed as additives in situ during compounding of carbon black filled polypropylene.

EXAMPLE 14

Polytetrafluoroethylene Filled Polyacetal

Twenty parts of Polytetrafluoroethylene (Teflon 340, E. I. duPont) filler, 79.9 parts acetal homopolymer (Delrin 107, E. I. duPont), were tumble blended with 0.1 parts of additive in a drum shaker and meter fed to the throat of a twin screw extruder having a relatively isothermal temperature profile of 190±5° C. throughout its 32:1 length/diameter barrel. At an L/D of 20:1, 20.0 parts by weight of PTFE powder were meter fed to the molten mix. The resultant extrudate was injection molded at approximately 185° C. to produce test specimens. The properties of composites produced using various additives are given in Table 14:

TABLE 14

| Additive | Tensile MPa ASTM D638 | Flexural Modulus GPa ASTM D790 | % Elongation ASTM D638 | % Equilibrium Water Absorption ASTM D570 | UL 94 Rating @ 0.12" |
|---|---|---|---|---|---|
| None | 54 | 2.3 | 22 | 0.2 | HB |
| C | 55 | 2.4 | 35 | 0.1 | V2 |
| A | 54 | 2.4 | 42 | 0.1 | V1 |
| N | 58 | 2.4 | 30 | 0.2 | V1 |
| AA | 49 | 2.0 | 27 | 0.2 | HB |
| AU | 50 | 2.0 | 27 | 0.2 | HB |
| AF | 50 | 1.9 | 20 | 0.1 | HB |

Note the products of the instant invention maintained physical properties of the composite while enhancing elongation and flame retardance, whereas prior art materials reduced physicals while enhancing elongation and did little to enhance flame retardance.

EXAMPLE 15

Carbon Fiber Filled Acetal Copolymer

Additives were mechanically blended in a ribbon blender at 0.15 wt. % based on a resin with a 20% (PAN) carbon fiber (Union Carbide) loaded acetal copolymer (Celcon C-400, Celanese Plastics) and fed to a twin screw extruder having a 190°-215° C. temperature profile. The physical and electrical properties of the resultant extrudates were measured on samples injection molded at 210° C. Results are given in Table 15:

TABLE 15

| Additive | Tensile MPa ASTM D638 | % Elongation ASTM D638 | Flexural Modulus GPa ASTM D790 | Notched Izod KJ/M ASTM D256 | Volume Resistivity Ohm-cm ASTM D257 |
|---|---|---|---|---|---|
| None | 57 | 5 | 6.1 | 0.06 | $8 \times 10^3$ |
| C | 59 | 23 | 6.4 | 0.15 | $6 \times 10^2$ |
| N | 63 | 41 | 6.7 | 0.15 | $5 \times 10^2$ |
| R | 55 | 28 | 6.2 | 0.20 | $9 \times 10^1$ |
| AG | 47 | 7 | 5.7 | 0.08 | $4 \times 10^3$ |
| AA | 48 | 9 | 5.5 | 0.10 | $8 \times 10^3$ |
| AR | 46 | 4 | 6.0 | 0.05 | $4 \times 10^4$ |

The results tabulated in Table 15 clearly establish the superiority of the products of the instant invention with respect to the parameters evaluated as compared to prior art additives.

EXAMPLE 16

PTFE Filled Acetals

Precompounded pellets of 20% PTFE filled acetal (Formalafil AC-80/TF/20, Wilson Fiberfill) together with 0.2 wt. % of the additive identified in Table 16 were mixed in a high shear mechanical blender and test samples injection molded at 200° C. prior to evaluation. The results are given in Table 16:

TABLE 16

| Additive | Tensile MPa ASTM D638 | % Elongation ASTM D638 | Flexural Modulus GPa ASTM D790 | Notched Izod KJ/M ASTM D256 |
|---|---|---|---|---|
| None | 59 | 20 | 2.5 | 0.06 |
| A | 58 | 23 | 2.3 | 0.07 |
| C | 62 | 40 | 2.2 | 0.15 |
| N | 62 | 55 | 2.2 | 0.20 |
| AA | 54 | 25 | 2.0 | 0.08 |
| AG | 52 | 28 | 1.9 | 0.08 |
| AH | 55 | 16 | 2.2 | 0.05 |
| AF | 55 | 15 | 2.2 | 0.05 |

EXAMPLE 17

Chlorinated Polyvinyl Chloride

Samples of chlorinated polyvinyl chloride (Geon 88935) were high shear blended with 0.2 wt. % additive prior to injection molding at 210° C. Results are given in Table 17.

TABLE 17

| Additive | Tensile MPa ASTM D638 | % Elongation ASTM D638 | Flexural Modulus GPa ASTM D790 | Notched Izod KJ/M ASTM D257 |
|---|---|---|---|---|
| None | 53 | 180 | 28 | 0.4 |
| A | 55 | 230 | 27 | 0.8 |
| G | 61 | 240 | 23 | 0.7 |
| J | 58 | 210 | 25 | 0.7 |
| K | 60 | 250 | 28 | 0.8 |
| M | 56 | 210 | 27 | 0.5 |
| N | 52 | 190 | 29 | 0.5 |
| AJ | 46 | 200 | 22 | 0.4 |
| AA | 45 | 170 | 25 | 0.5 |
| AL | 42 | 190 | 25 | 0.5 |
| AR | 50 | 200 | 24 | 0.3 |
| AP | 50 | 160 | 28 | 0.3 |

Note that the products of the instant invention provided superior impact properties as compared to those imparted by prior art products.

EXAMPLE 18

Ethyl Cellulose

Samples of ethyl cellulose (Hercules type T) and 0.5 wt. % of the indicated additive were ball milled for four hours followed by extrusion at 230° C. The results of water absorption (ASTM D570) tests on extruded specimens are given in Table 18:

TABLE 18

| Additive | 24 Hour Water Absorption ASTM D570 | % Equilibrium Water Absorption ASTM D570 |
|---|---|---|
| None | 1.2 | 1.8 |
| C | 0.8 | 1.2 |
| D | 0.4 | 1.0 |
| N | 0.5 | 0.9 |
| AA | 0.9 | 1.8 |
| AG | 0.7 | 1.4 |
| AF | 0.9 | 1.8 |

The results given in Table 18 clearly establish the superiority of the products of the instant invention vs. their prior art analogs as water absorption inhibitors in ethyl cellulose.

EXAMPLE 19

Clay Filled Nylon

Samples of 50% clay (Icecap K, Burgess Corp.) filled Nylon 6 (Capron 8202, Allied Corp.) were prepared by meter feeding simultaneously clay, nylon and additive (at 0.2 wt. % on mix) as a 65% concentrate on silica, to the throat of a 32:1 twin screw extruder, operating at 250°–265° C. Test samples were injection molded at 250° C. Results are given in Table 19:

TABLE 19

| Additive | Tensile MPa ASTM D638 | % Elongation ASTM D638 | Flexural Modulus GPa ASTM D790 | Notched Izod KJ/M ASTM D256 | % 24 Hour Water Absorption ASTM D570 |
|---|---|---|---|---|---|
| None | 90 | 4 | 6.7 | 0.03 | 5.4 |
| U | 124 | 70 | 7.5 | 0.45 | 2.6 |
| K | 102 | 32 | 6.7 | 0.20 | 1.8 |
| N | 95 | 25 | 6.5 | 0.20 | 1.7 |
| AQ | 95 | 10 | 6.2 | 0.15 | 5.2 |
| AP | 100 | 5 | 7.0 | 0.05 | 5.4 |

Note the significant improvement in elongation, impact and moisture absorption retardation imparted by the products of the instant invention as compared to those produced by prior art products.

EXAMPLE 20

Acrylonitrile-Styrene-Butadiene

Samples of precompounded acrylonitrile-styrene-butadiene copolymer (Cycolac KJM, Borg-Warner) were tumble blended in a drum tumbler with 0.2 wt. % of additive and thereafter injection molded at 270° C. Flame retardancy improvement is shown in Table 20.

TABLE 20

| Additive | Flame Retardant Rating UL-94 | | |
|---|---|---|---|
|  | 0.12" | 0.058" | 0.02" |
| None | V0 | V1 | V1 |
| H | V0 | V0 | V1 |
| G | V0 | V0 | V0 |
| K | V0 | V0 | V0 |
| N | V0 | V0 | V0 |
| AA | V0 | V0 | V1 |
| AJ | V0 | V1 | V1 |

Note the greater efficacy of products of the instant invention and as compared to their prior art analogs, as flame retardant enhancers in ABS.

EXAMPLE 21

Carbon Fiber Filled ABS

This example teaches the superiority of the products of the instant invention as compared to those of the prior art with respect to electrical, physical, rheological and water absorption resistance enhancements when employed as additives in the extrusion (at 250° C.) in 30% PAN carbon fiber (Union Carbide) loaded ABS (Lustran ABS-545, Monsanto). The samples were injection molded at 240° C. for evaluation. The results and the additives employed are shown in Table 21:

TABLE 21

| Additive | Tensile MPa ASTM D638 | Flexural Modulus GPa ASTM D790 | Notched Izod KJ/M ASTM D256 | % 24 Hour Water Absorption ASTM D570 | MFI g/10 min. ASTM D1238 | Volume Resistivity Ohm-cm ASTM D257 |
|---|---|---|---|---|---|---|
| None | 86 | 106 | 0.04 | 0.4 | 0.002 | $3 \times 10^3$ |
| J | 94 | 105 | 0.10 | 0.04 | 0.05 | $1 \times 10^2$ |
| K | 101 | 112 | 0.10 | 0.08 | 0.03 | $8 \times 10^2$ |
| N | 90 | 101 | 0.09 | 0.15 | 0.04 | $3 \times 10^2$ |
| Q | 86 | 105 | 0.07 | 0.10 | 0.01 | $4 \times 10^2$ |
| AA | 72 | 89 | 0.05 | 0.2 | 0.02 | $9 \times 10^2$ |
| AJ | 78 | 90 | 0.05 | 0.2 | 0.02 | $7 \times 10^2$ |

Note that improvements in impact, water absorption, electrical and flow properties were substantially greater when products of the instant invention were employed as compared to those of the prior art.

EXAMPLE 22

Phenolic Molding Compound

Additives at 0.3 wt. % were first converted to 65% concentrates on silica powder then mixed intensively (Wellex) with the preformed precompounded nylon fiber reinforced compression molded phenolic (Budd Polychem 155) molding compound prior to compression molding at 175° C. of test specimens. Results are given in Table 22:

TABLE 22

| Additive | Tensile MPa ASTM D638 | Flexural Strength at Yield MPa ASTM D790 | Flexural Modulus GPa ASTM D790 | Compression Strength MPa ASTM D695 | Notched Izod KJ/M ASTM D256 |
|---|---|---|---|---|---|
| None | 52 | 83 | 3.7 | 150 | 0.03 |
| D | 54 | 89 | 3.7 | 172 | 0.10 |
| F | 59 | 86 | 3.4 | 190 | 0.15 |
| B | 67 | 85 | 3.8 | 175 | 0.13 |
| T | 62 | 87 | 3.6 | 180 | 0.09 |
| U | 82 | 89 | 3.9 | 194 | 0.18 |
| AR | 47 | 83 | 3.2 | 148 | 0.04 |
| AL | 42 | 85 | 3.4 | 150 | 0.05 |
| AP | 45 | 80 | 3.4 | 151 | 0.04 |
| AT | 50 | 80 | 2.9 | 142 | 0.03 |

The data in Table 22 clearly shows the enhanced performance of the products of the instant invention as compared to prior art with respect to compressive strength and impact property enhancement when employed as low level additive in nylon filled phenolic molding compound.

EXAMPLE 23

Conductive Polyphenylene Oxide

Liquid additives were independently fed at the throat of an extruder as a dryblend on the modified polyphenylene oxide (Noryl 731—General Electric Co.), and 20% carbon black (Vulcan P—Cabot Corp.) was fed downstream to the polymer melt in a three stage 10 barrel Berstoff extruder having a 270°-300° C. profile. The test samples which contained 0.3 wt. % of additive based on total formulation were injection molded at 285° C. Results of these evaluations are given in Table 23:

TABLE 23

| Additive | Tensile MPa ASTM D638 | % Elongation ASTM D638 | Flexural Modulus GPa ASTM D790 | Notched Izod KJ/M ASTM D256 | Volume Resistivity Ohm-cm ASTM D257 |
|---|---|---|---|---|---|
| None | 41 | 2 | 2.9 | 0.02 | 5000 |
| A | 46 | 39 | 3.1 | 0.09 | 400 |
| K | 44 | 42 | 3.5 | 0.07 | 90 |
| Q | 40 | 65 | 3.2 | 0.09 | 300 |
| AA | 40 | 4 | 2.7 | 0.02 | 900 |
| AJ | 38 | 8 | 2.5 | 0.03 | 700 |
| AR | 34 | 12 | 2.8 | 0.03 | 1000 |
| AT | 37 | 3 | 2.4 | 0.02 | 1000 |

The data in Table 23 clearly establish the superiority of the products of the instant invention as compared to those of the prior art when employed as additives in the extrusion of carbon black filled modified polyphenylene oxide for the purposes of conductivity, elongation and impact property enhancements.

EXAMPLE 24

Injection Molded PPO

Modified polyphenylene oxide (Noryl N-300—General Electric Co.) pellets were tumble blended with additive in a pneumatic conveyer system and screw injection molded at 270° C. to product test specimens. The results of independent additions of various additives (at 0.3 wt. %) are given in Table 24:

TABLE 24

| Additive | Tensile MPa ASTM D638 | Flexural Modulus GPa ASTM D790 | % Elongation ASTM D638 | Notched Izod KJ/M ASTM D256 | Heat Distortion Temp 1.81 MPa ASTM D648 |
|---|---|---|---|---|---|
| None | 83 | 4.0 | 15 | 0.16 | 150 |
| M | 89 | 4.1 | 84 | 0.29 | 150 |
| N | 94 | 3.8 | 90 | 0.34 | 148 |
| K | 82 | 4.4 | 72 | 0.43 | 152 |
| H | 83 | 4.2 | 61 | 0.45 | 154 |
| AB | 77 | 3.7 | 18 | 0.18 | 141 |
| AK | 79 | 3.5 | 20 | 0.22 | 137 |
| AP | 68 | 3.3 | 16 | 0.30 | 143 |
| AS | 81 | 3.7 | 15 | 0.25 | 146 |
| AT | 80 | 3.8 | 21 | 0.15 | 141 |

Note that the products of the instant invention, when employed as minor additives in PPO injection molding, not only provided superior elongation and impact improvement as compared to the prior art, but simultaneously gave less heat distortion temperature loss than did the prior art analogs.

EXAMPLE 25

Carbon Fiber-Filled Polystyrene

Test samples containing 30% PAN carbon fiber were produced by feeding a dryblend of polystyrene (Cosden 550) resin and additive (0.3 wt. %) to the throat of a twin screw (W&P-12 barrel) extruder and feeding carbon fiber downstream to the melt (extrusion at 210°–240° C.) followed by injection molding the extrudate at 230° C. Results are given in Table 25:

TABLE 25

| Additive | Tensile MPa ASTM D638 | Flexural Modulus GPa ASTM D790 | Notched Izod KJ/M ASTM D256 | Volume Resistivity Ohm-cm ASTM D257 |
|---|---|---|---|---|
| None | 95 | 1.9 | 0.01 | $1 \times 10^3$ |
| A | 106 | 1.8 | 0.07 | $3 \times 10^2$ |
| S | 97 | 2.1 | 0.10 | $4 \times 10^2$ |
| D | 114 | 2.3 | 0.14 | $8 \times 10^1$ |
| L | 108 | 1.7 | 0.08 | $3 \times 10^2$ |
| AG | 81 | 1.8 | 0.02 | $9 \times 10^2$ |
| AF | 69 | 1.6 | 0.02 | $1 \times 10^3$ |
| AH | 76 | 1.7 | 0.01 | $7 \times 10^2$ |

Note the products of the instant invention, when employed as minor additives in the extrusion of carbon fiber filled polystyrene, gave superior tensile, impact and electrical properties as compared to both the control and the prior art, whereas the prior art analogs had far less beneficial effects (if any) and each instance tested degraded tensile strength.

EXAMPLE 26

MICA Filled Polycarbonate

This example demonstrates the superiority of the products of the instant invention as compared to those of the prior art with respect to rheological and physical property enhancement when employed as minor additives in 15% mica filled resin.

Additive (0.2 wt. %) coated polycarbonate resin (Lexan EM—General Electric Co.) was fed at the throat of a three stage, 10 barrel Berstoff extruder and 15 wt. % (based on final compound) of mica (Suzerite—Martin Marietta Corp.) was fed downstream to the melt via a crammer feeder. The extrusion was performed at 300°–330° C. and the extrudate injection molded at 320° C. to produce test specimens. Results are given in Table 26.

TABLE 26

| Additive | Tensile MPa ASTM D638 | % Elongation ASTM D638 | Notched Izod KJ/M ASTM D256 | Melt Flow Index ASTM D1238 |
|---|---|---|---|---|
| None | 55 | 11 | 0.15 | 0.7 |
| A | 59 | 62 | 0.35 | 0.9 |
| U | 73 | 105 | 0.80 | 4.9 |
| S | 54 | 46 | 0.40 | 2.1 |
| D | 53 | 50 | 0.40 | 2.8 |
| AG | 50 | 15 | 0.20 | 0.8 |
| AH | 42 | 20 | 0.20 | 0.8 |
| AF | 46 | 16 | 0.20 | 0.7 |
| AQ | 50 | 31 | 0.30 | 0.8 |

Note the products of the instant invention provide simultaneous substantial improvements in impact, elongation (and in come cases) melt flow. The products of the prior art displayed only modest enhancement of measured properties (if any), and in each instance, tested degraded tensile strength when employed in situ as additives in the extrusion of mica filled polycarbonate.

EXAMPLE 27

Polyethylene and Polybutylene Terephthalate Alloy

Blends of 50 parts of polyethylene terphthalate (Tenite 6857—Eastman), 48 parts of polybutylene terphthalate (Gafite 1600-A—GAF), 2 parts of titanium dioxide (R-901—Dupont), and 0.12 parts of the specified additive were extruded in a single stage 24:1, L:D Prodox extruder at 275°–305° C. followed by injection molding of physical test specimens at 300° C. in a ram type molding unit. A control test specimen was also prepared by melt blending in a nitrogen blanketed autoclave. The results of these evaluations are given in Table 27:

TABLE 27

| Additive | Intrinsic Viscosity (poise) | Melt Flow Index ASTM D1238 | Notched Izod KJ/M ASTM D256 |
|---|---|---|---|
| None Melt Blend | 2.38 | 3.2 | 0.02 |
| None Extruded | 2.11 | 3.8 | 0.04 |
| J | 2.48 | 4.2 | 0.14 |
| R | 2.46 | 4.5 | 0.16 |
| T | 2.50 | 4.1 | 0.18 |
| AA | 2.21 | 3.7 | 0.07 |
| AN | 2.33 | 3.8 | 0.07 |
| AR | 2.09 | 3.7 | 0.06 |
| AM | 2.11 | 3.8 | 0.06 |

The experimental results tabulated in Table 27 clearly demonstrate that the products of the instant invention minimize thermal degradation of PBT/PET alloy far more effectively than do prior art analogs which have previously been shown to be effective process aids at lower temperatures.

EXAMPLE 28

Polyether-Polyol Derived Polyurethane

This example demonstrates the enhanced solvolytic stability of the products of the instant invention as compared to those of the prior art when employed as co-catalysts in thermoset polyurethane (Pellethane CPR 135-50D—Upjohn).

The additives were added at 0.5 wt. % on polyol component and the mix aged at 40° C. under nitrogen for the period indicated prior to isocyanate component addition. Results are given in Table 28:

TABLE 28

| Additive | Aged Hr | Tensile MPa ASTM D638 | % Elongation ASTM D638 | Flexural Modulus GPa ASTM D790 | Cure Time Min. |
|---|---|---|---|---|---|
| None | 0.05 | 21 | 350 | 0.09 | 54 |
| None | 24 | 21 | 360 | 0.09 | 55 |
| U | 0.05 | 37 | 390 | 0.35 | 21 |
| U | 24 | 39 | 400 | 0.42 | 19 |
| Q | 0.05 | 31 | 420 | 0.21 | 68 |
| Q | 24 | 29 | 400 | 0.20 | 66 |
| AQ | 0.05 | 29 | 390 | 0.40 | 23 |
| AQ | 24 | 23 | 350 | 0.10 | 22 |
| AJ | 0.05 | 33 | 390 | 0.19 | 69 |
| AJ | 24 | 23 | 360 | 0.09 | 57 |

Note the initial tensile and flexural modulus property improvements and cure time control conferred by the addition of Additives AQ and AJ were comparable to those of their neoanalogs U and Q, respectively. However, the comparability of the former was substantially diminished within 24 hours, thus demonstrating the enhanced solvolytic stability of the products of the instant invention as compared to the prior art.

EXAMPLE 29

Polyurethane

This example demonstrates the superior thermal/solvolytic stability of the products of the instant invention as compared to those of the prior art with respect to polyester polyurethanes (Pellethane 2102-80HE—Upjohn) when employed in both casting and extrusion modes. For extrusion evaluation, the components were tumble blended with 0.4% additive and extruded at 205°–220° C. using a two stage vented 24:1 Prodox extruder; followed by injection molding of test specimens at 210° C.

Casting was accomplished by dissolving the resin in anisole at ambient temperature to produce a 20% solution containing 0.5% additive followed by solvent evaporating (after appropriate aging) in vacuo at 80° C. to produce castings from which test samples were die cut for evaluation. Results are given in Table 29A and 29B, respectively:

TABLE 29A

EXTRUDED THERMOPLASTIC POLYESTER POLYURETHANE

| Additive | Tensile MPa ASTM D638 | % Elongation ASTM D638 | Flexural Modulus GPa ASTM D790 | Hardness Shore A |
|---|---|---|---|---|
| None | 45 | 550 | 0.05 | 83 |
| U | 58 | 480 | 0.22 | 87 |
| T | 48 | 540 | 0.12 | 84 |
| B | 46 | 550 | 0.13 | 84 |
| AQ | 41 | 590 | 0.05 | 83 |
| AT | 40 | 550 | 0.05 | 83 |
| AR | 44 | 510 | 0.05 | 82 |

Note the products of the instant invention provide enhancement of flexural modulus when used as additives in extruded polyester polyurethane, whereas their non-neoanalogs are ineffective.

TABLE 29B

CAST POLYESTER POLYURETHANE

| Additive | Aging Time Hr. | Tensile MPa ASTM D638 | % Elongation ASTM D638 | Flexural Modulus GPa ASTM D790 | Hardness Shore A |
|---|---|---|---|---|---|
| None | 0.1 | 48 | 600 | 0.05 | 83 |
| None | 168 | 48 | 600 | 0.05 | 82 |
| U | 0.1 | 61 | 580 | 0.31 | 88 |
| U | 168 | 60 | 570 | 0.29 | 88 |
| T | 0.1 | 52 | 600 | 0.13 | 83 |
| T | 168 | 52 | 600 | 0.12 | 83 |
| B | 0.1 | 54 | 600 | 0.15 | 83 |
| B | 24 | 50 | 600 | 0.11 | 83 |
| B | 168 | 50 | 600 | 0.09 | 83 |
| AQ | 0.1 | 50 | 600 | 0.09 | 88 |
| AQ | 24 | 49 | 600 | 0.05 | 83 |
| AT | 0.1 | 51 | 600 | 0.08 | 82 |
| AT | 24 | 47 | 600 | 0.05 | 82 |
| AR | 0.1 | 50 | 600 | 0.10 | 83 |
| AR | 24 | 50 | 600 | 0.04 | 82 |

Note the products of the instant invention enhance the properties of cast polyester polyurethane in anisole solution for at least 168 hrs., whereas their prior art analogs failed within one-seventh of said period. This demonstrates the superior solvolysis resistance of the products of the instant invention.

EXAMPLE 30

Polyurethane Adhesive

The effect of 0.25% of various neoalkoxy compounds on a hot melt polyurethane adhesive (Compo 1479) for adhering rigid PVC to nylon substrates is shown in Table 30.

TABLE 30

| Additive | 180° Peel Strength (kN/m) |
|---|---|
| None | 0.78 |
| V | 0.92 |
| N | 0.86 |
| K | 1.49 |
| U | 2.91 |
| Z5 | 2.68 |
| Z6 | 4.20 (CF) |

(CF) Cohesive Failure of Adhesive

The above data show the effect of the neoalkoxy compounds on the polyurethane adhesive. While all of the titanate compounds improve the adhesivity to some degree, the titanate, additive U, and the zirconate compounds enhance performance to the greatest extent.

EXAMPLE 31

Two-Component Urethane Adhesion

The effect 0.2% of of the neoalkoxy compounds on the adhesion of Bostic No. 7772 R21 two-component urethane to polypropylene substrate is shown in the Table 31A below. The Table 31B below shows the effect of 0.25% on two-component low pressure RIM urethane adhesion to semirigid PVC.

TABLE 31A

| Additive | Substrate | Lap Shear Strength (MPa) |
|---|---|---|
| None | Polypropylene | 0.95 |
| C | " | 2.70 |
| V | " | 2.40 |
| N | " | 3.20 |
| K | " | 1.50 |
| U | " | 1.10 |
| Z2 | " | 2.40 |

TABLE 31B

| Additive | Substrate | Lap Shear Strength (MPa) |
|---|---|---|
| None | Semirigid PVC | 2.90 |
| C | " | 3.20 |
| V | " | 3.40 |
| N | " | 3.60 |
| K | " | 4.70 |
| U | " | 7.50 |
| Z5 | " | 6.20 |
| Z6 | " | 10.50 (CF) |

(CF) Cohesive Failure of Adhesive

Again, it will be noted that both the titanates and the zirconates markedly improve the shear strength of the systems. Particularly outstanding is the zirconate additive Z6.

EXAMPLE 32

Urethane Adhesives

This example shows the effect of the neoalkoxy titanates and zirconates on Uralite 5738 A/B urethane adhesives for Upjohn Pellethane 2103-80WC to ABS, nylon 6/6 and aluminum. 0.25% of the neoalkoxy compound is used. The results are shown in the following table:

TABLE 32

| Additive | Substrate | Lap Shear Strength (MPa) |
|---|---|---|
| None | ABS (Monsanto) Lustran 545 | 6.50 |
| V | " | 8.20 |
| N | " | 10.10 |
| K | " | 10.40 |
| U | " | 10.90 |
| Z5 | " | 9.60 |
| Z6 | " | 15+ (CF) |
| None | Nylon 6/6 (Celanese) N-186 | 8.40 |
| K | " | 10.20 |
| U | " | 11.60 |
| Z5 | " | 11.00 |
| Z6 | " | 9.10 |
| None | Degreased Aluminum (Q Panel) | 5.10 |
| V | " | 6.20 |
| N | " | 7.40 |
| U | " | 9.50 |

(CF) Cohesive Failure of Adhesive

The foregoing table shows the improved lap shear strength achieved by the addition of the compounds of the invention.

EXAMPLE 33

Thermoplastic Urethane

The addition of 0.3% neoalkoxy compounds on the physical properties of thermoplastic urethane extrusion profiles is shown in the following table.

TABLE 33

| Additive | Elongation at Break % | Tensile Strength at Break (MPa) |
|---|---|---|
| None | 640 | 35 |
| C | 780 | 35 |
| V | 810 | 39 |
| N | 760 | 42 |
| K | 650 | 45 |
| U | 600 | 52 |
| Z5 | 620 | 50 |
| Z6 | 580 | 55 (DC) |

(DC) Severe Discoloration

The above table shows that, generally speaking, the elongation to break is improved most markedly by the neoalkoxy titanates, while the tensile strength of the material is improved to the greatest extent by the neoalkoxy zirconates.

EXAMPLE 34

RIM Molded Urethane

This example shows the effect of 0.2% neoalkoxy titanates and neoalkoxy zirconates on the physical properties of RIM molded polyurethane (Texaco RIM TEX 140).

TABLE 34

| Additive | % Elongation at Break | Flexural Modulus (GPa) | Tensile Strength at Break (MPa) |
|---|---|---|---|
| None | 125 | 1.05 | 34.5 |
| C | 155 | 1.07 | 35.0 |
| N | 140 | 1.12 | 36.0 |
| K | 160 | 1.10 | 33.0 |
| U | 110 | 1.55 | 51.0 |
| Z5 | 125 | 1.43 | 46.0 |

Compared to the controls, all of the neoalkoxy compounds improved the percent elongation at break and the flexural modulus. Tensile strength at break was also greatly enhanced by the addition of the last two compounds listed.

EXAMPLE 35

Glass-Reinforced Peroxide-Cured Polyester

In this example, formulations containing 70 parts by weight of polyester resin (S-600 Silmar Corp.); 30 parts of 1 mm milled bare glass (Owens Ill.); 0.5 part of a catalyst consisting of benzoyl peroxide and 200 ppm of cobalt acetylacetonate; and 0.14 part of the additives shown in the table below were cured for 10 minutes at 150° C. and post-cured for 2 hours at 100° C. The properties of the cured formulations are shown below. In addition to the control, the use of silane additives is also illustrated.

TABLE 35

| Additive | Ten. Str. MPa | Elong. % | Flex. Str. MPa | Flex. Mod. GPa | Compr. Str. MPa | UL94 Rating @ 0.06 |
|---|---|---|---|---|---|---|
| None | 135 | 2 | 193 | 8.3 | 124 | $V_1$ |
| V | 132 | 6 | 216 | 8.0 | 136 | $V_1$ |
| N | 147 | 6 | 221 | 8.0 | 132 | $V_0$ |
| K | 142 | 8 | 229 | 7.9 | 140 | $V_0$ |

TABLE 35-continued

| Additive | Ten. Str. MPa | Elong. % | Flex. Str. MPa | Flex. Mod. GPa | Compr. Str. MPa | UL94 Rating @ 0.06 |
|---|---|---|---|---|---|---|
| Z3 | 146 | 5 | 220 | 8.7 | 151 | $V_0$ |
| Z4 | 154 | 3 | 236 | 9.2 | 157 | $V_0$ |
| A-174[a,b] | 138 | 2 | 199 | 9.1 | 131 | $V_1$ |
| A-1100[a,c] | 152 | 1 | 210 | 9.9 | 142 | $V_1$ |
| A-172[a,d] | 137 | 3 | 204 | 9.2 | 137 | $V_1$ |
| A-1100 | 139 | 2.5 | 195 | 8.2 | 125 | $V_1$ |
| A-174 | 136 | 2.5 | 197 | 8.3 | 127 | $V_1$ |

Note:
[a]Glass pretreated with silane in 95% ethanol and dried.
[b]A-174 - Union Carbide, gamma-Methacryloxypropyltrimethoxy silane
[c]A-1100 - Union Carbide, gamma-Aminopropyltrimethoxysilane
[d]A-172 - Union carbide, Vinyl-tris(2-methoxyethoxy) silane The above data clearly show that the additives of the invention improve certain of the physical properties of the cured formulations and in most instances improve the flame-resistance of the material. The neoalkoxy zirconate compounds are particularly effective in improving the tensile strength, the flexural strength, and the compressive strength of the polyester. In contrast, the silanes of the prior art do not improve the flame-resistance of the material and were considerably less effective in improving the physical properties of the polyester.

EXAMPLE 36

Peroxy-Cured Glass-Reinforced Polyester

Formulations containing 70 parts by weight of a polyester resin (Stypol 40-3904, Freeman Chemical); 30 parts of chopped bare glass; 0.5 part of a catalyst comprising methylethyl ketone peroxide and 100 ppm of cobalt (naphthenate); and 0.14 part of the additives shown below were cured at ambient temperature and post-cured for 2 hours at 120° C. The results obtained are shown in the table below.

TABLE 36

| Additive | Gel/Cure Time, Min. | Ten. Str. MPa D638 | Flex. Mod. GPa D790 | Flex. Str. MPa D790 | Compr. Str. MPa D695 | Notched Izod KJ/M D256 | % Elong. D638 |
|---|---|---|---|---|---|---|---|
| None | 52/79 | 125 | 8.3 | 187 | 122 | 0.072 | 2.5 |
| V:AA[a] | 69/98 | 121 | 8.0 | 204 | 130 | 0.091 | 3.7 |
| N:AA[a] | 54/81 | 127 | 8.3 | 196 | 135 | 0.094 | 3.9 |
| K:AA[a] | 56/82 | 142 | 8.5 | 216 | 146 | 0.17 | 4.8 |
| U:AA[a] | 48/71 | 156 | 8.9 | 221 | 154 | 0.087 | 2.8 |
| Z3 | 40/61 | 142 | 8.1 | 194 | 136 | 0.092 | 3.2 |
| Z4 | 44/69 | 159 | 9.7 | 228 | 147 | 0.18 | 3.7 |
| Z5 | 38/57 | 149 | 10.6 | 217 | 164 | 0.094 | 4.2 |

Note:
[a]Additive contains 50% acetylacetone by weight.

This table shows the surprising advantage of using the neoalkoxy zirconates of the invention as coupling agents in these compositions. In contrast to the control and the material containing the neoalkoxy titanate coupling agent, the gel and cure time with the neoalkoxy zirconates were markedly reduced. This clearly shows the accelerating effect of these latter compounds. In addition, the coupling agents of the instant invention also selectively improve the physical properties of the reinforced polyester.

EXAMPLE 37 Peroxide-Cured CaCO3 Filled Polyester

Formulations were prepared containing 30 parts by weight of a synthetic marble mix polyester resin (Stypol 40-5727, Freeman Chemical); 70 parts of calcium carbonate in the form of ground marble dust (Micro White 50, Sylacauga); 0.5 part of a catalyst comprising methylethyl ketone peroxide; and 0.2 part of the additives shown below, added to the resin prior to the addition of the marble dust. The compositions were cured at ambient temperature and their physical properties measured. The results are shown in the following table:

TABLE 37

| Additive | Gel/Cure Time Min. | Ten. Str. MPa | Flex. Str. MPa | Flex. Mod. GPa | Compr. Str. MPa D695 | Uncatalyzed Visc. @ 25° C. Poise × $10^6$ |
|---|---|---|---|---|---|---|
| None | 58/92 | 62 | 139 | 9.0 | 152 | 14 |
| V:AA[a] | 79/107 | 70 | 149 | 8.2 | 165 | 0.9 |
| N:AA[a] | 62/94 | 69 | 142 | 8.6 | 161 | 0.4 |
| K:AA[a] | 60/97 | 77 | 160 | 8.7 | 156 | 0.7 |
| Z2 | 38/72 | 72 | 143 | 9.7 | 141 | 12 |
| Z3 | 31/67 | 68 | 151 | 9.5 | 136 | 8 |
| Z4 | 42/87 | 84 | 169 | 10.3 | 172 | 10 |

Note:
[a]Additive contains 50% acetylacetone by weight.

The above data clearly show that the neoalkoxy titanates tend to retard the cure of the polyester, while the neoalkoxy zirconates function as accelerators. The additives of the invention improve the tensile strength and the compressive strength of the formulations in most instances.

EXAMPLE 38

Peroxide-Cured Polyester Clear Coat

Formulations containing 100 parts by weight of polyester resin (Hetron 700C, Ashland Chemical Co.); 0.5 part of methylethyl ketone peroxide catalyst; and 0.4 part of the additives shown in the table below were cured at ambient temperature. The gel and cure times and the physical properties of the cured formulations are shown in the table below.

TABLE 38

| Additive | Gel/Cure Time, Min. | Ten. Str. Break MPa D638 | % Elong. @ Break D638 | Ten. Mod. GPa D638 | Flex. Mod. GPa D740 | Flex. Str. MPa D790 | Notched Izod KJ/M D256 |
|---|---|---|---|---|---|---|---|
| None | 41/54 | 38 | 4 | 2.8 | 2.9 | 110 | 0.014 |
| C | 240/— | — | — | — | — | — | — |
| V | 84/117 | 46 | 7 | 2.4 | 2.6 | 132 | 0.19 |
| N | 72/101 | 49 | 8 | 2.6 | 2.7 | 146 | 0.26 |
| K | 240/— | — | — | — | — | — | — |
| U | 240/— | — | — | — | — | — | — |
| Z1 | 23/31 | 36 | 13 | 2.1 | 2.2 | 108 | 0.22 |
| Z2 | 24/34 | 49 | 10 | 2.5 | 2.7 | 136 | 0.31 |
| Z3 | 19/26 | 46 | 15 | 2.5 | 2.7 | 155 | 0.28 |
| Z4 | 22/30 | 57 | 12 | 2.6 | 3.2 | 161 | 0.35 |
| Z5 | 25/31 | 42 | 19 | 2.7 | 3.0 | 172 | 0.26 |

The data above show the severe retarding effect on the peroxide cure of the neoalkoxy titanates. Certain of these titanates substantially prevent the curing of the material, while others merely retard the reaction. In contrast, each and every one of the neoalkoxy zirconates tested markedly accelerated the time to gel and the cure time. Furthermore, the elongation to break of the compounds cured in the presence of the neoalkoxy zirconates shows that higher molecular weights were achieved. Substantial improvements in notched Izod values and, in certain instances, flexural strength and tensile strength, are also apparent.

EXAMPLE 39

Compression Molded SMC Structural Polyester

Formulations containing 100 parts by weight of a polyester resin (Armco 8057 SMC 70% carbon); 0.5 part of p-chloro-perbenzoate catalyst; and 0.4 part of the additives shown in the table below were cured for 1 minute at 200° C. and thereafter cured for 8 hours at 150° C. The table below shows the physical properties of the cured material.

TABLE 39

| Additive | Ten. Str. | Flex. Mod. GPa | Flex. Str. MPa | Notched Izod KJ/M | HDT 1.18 MPa @ °C. D648 |
|---|---|---|---|---|---|
| None | 595 | 69 | 674 | 1.06 | 208 |
| V | 580 | 63 | 740 | 1.35 | 202 |
| N | 592 | 64 | 752 | 1.31 | 201 |
| K | 583 | 62 | 731 | 1.46 | 206 |
| U | 634 | 69 | 765 | 1.26 | 216 |
| Z3 | 631 | 71 | 743 | 1.19 | 214 |
| Z4 | 628 | 72 | 736 | 1.23 | 221 |
| Z5 | 662 | 79 | 781 | 1.64 | 235 |

The data clearly show that the neoalkoxy compounds of the invention improve the flexural strength and notched Izod of the cured composition. Improvements are also shown in selective additives, particularly for the zirconates, in the tensile strength and HTD value.

EXAMPLE 40

Perbenzoate-Cured Polyester Potting Compounds

In this example, formulations were prepared containing 100 parts by weight of a premix glass-carbon static dissipating BMC polyester potting compond (Premi-Glas BMC-ESD); 0.5 part of t-butyl perbenzoate catalyst; and 0.2 part of the additives shown in the following table. The formulations were cured for 35 sec. at 220° C. and post-cured for 4 hours at 150° C. The following table shows the physical and electrical properties of the cured formulations.

TABLE 40

| Additive | Tens. Str. MPa | Elong. % | Flex. Mod. GPa | Flex. Str. MPa | Compr. Str. MPa | Notched Izod KJ/M | Volume Resistivity Ohm-cm |
|---|---|---|---|---|---|---|---|
| None | 28 | 2.1 | 9.6 | 83 | 124 | 0.27 | $2 \times 10^2$ |
| V | 27 | 3.4 | 9.2 | 107 | 134 | 0.45 | 83 |
| N | 34 | 3.7 | 9.4 | 116 | 137 | 0.52 | 69 |
| K | 31 | 4.1 | 9.5 | 109 | 131 | 0.50 | 7 |
| Z2 | 41 | 3.2 | 9.7 | 131 | 146 | 0.62 | 47 |
| Z4 | 46 | 3.0 | 9.9 | 128 | 162 | 0.55 | 12 |
| A-1100[a] | 30 | 2.0 | 9.8 | 96 | 129 | 0.25 | $2.4 \times 10^2$ |
| A-174[b] | 33 | 2.0 | 9.7 | 87 | 125 | 0.36 | $3.1 \times 10^3$ |

Note:
[a]A-1100 - Union Carbide, gamma-Aminopropyltrimethoxy silane
[b]A-174 - Union Carbide, gamma-Methacryloxypropyltrimethoxy silane The above data clearly show that the compounds of the invention may improve the tensile strength, elongation, flexural strength, compression, and notched Izod values of the formulations.

EXAMPLE 41

Glass-Reinforced Peroxide-Cured Polyester

In this example, formulations were prepared from 100 parts by weight of a BMC polyester resin (Dielectrite 44-1 BMC, Industrial Dielectric), 1 part of benzoyl peroxide catalyst, and 0.3 part of the additives shown below. The formulations were cured for 10 minutes at 180° C. and post-cured for 2 hours at 150° C. The physical and electrical properties of the cured compositions are shown in the table below.

TABLE 41

| Additive | Flex. Mod. MPa | Flex. Str. MPa | Compr. Str. MPa | Notched Izod KJ/M | Dielectric Str. MV/M | Hardness Barcol |
|---|---|---|---|---|---|---|
| None | 13.1 | 125 | 154 | 0.26 | 13.2 | 34 |
| V | 12.2 | 138 | 161 | 0.38 | 13.5 | 33 |
| N | 12.9 | 135 | 168 | 0.42 | 13.7 | 35 |
| K | 11.7 | 152 | 172 | 0.59 | 13.5 | 34 |
| Z3 | 13.0 | 151 | 163 | 0.41 | 15.1 | 39 |
| Z4 | 13.4 | 162 | 167 | 0.64 | 15.0 | 42 |
| Z5 | 13.9 | 174 | 159 | 0.70 | 14.2 | 47 |

The above data clearly show that the cured material containing the neoalkoxy zirconates have substantially improved dielectric strength as compared to the cured composition without an additive or those containing the neoalkoxy titanates. All of the neoalkoxy titanates, however, selectively increase the physical strength of the polyester compound.

EXAMPLE 42

Cured Polyester Clear Coat

In this example, compositions containing 100 parts by weight of polyester resin (Aropol 7362, Ashland), 0.5 part of methylethyl ketone peroxide, and 0.2 part of the additives shown below were cured at ambient temperature and post-cured for 24 hours at 50° C. The table below shows the physical properties of the cured material.

TABLE 42

| Additive | Ten. Str. MPa | Elong. % | Flex. Mod. GPa | Flex. Str. MPa |
|---|---|---|---|---|
| None | 38 | 1.5 | 10.5 | 77 |
| N:AA | 43 | 8.4 | 9.4 | 86 |
| K:AA | 47 | 6.7 | 9.2 | 91 |
| Z2 | 51 | 4.2 | 10.2 | 84 |
| Z3 | 48 | 4.9 | 10.8 | 86 |
| Z4 | 54 | 4.3 | 10.1 | 92 |
| Z5 | 72 | 3.1 | 13.1 | 95 |

It is apparent that the addition of the neoalkoxy compounds of the invention improved the tensile strength and percent elongation of the polyester clear coat, as well as the flexural strength. In addition, the last-named zirconate improved the flexural modulus of the composition.

What is claimed is:

1. An organo-zirconate having the formula:

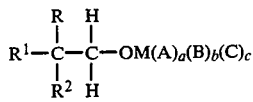

wherein M is zirconium, R, $R^1$ and $R^2$ are each a monovalent alkyl, alkenyl, alkynyl, aralkyl, aryl or alkaryl group having up to 20 carbon atoms, or a halogen or ether substituted derivative thereof, and, in addition, $R^2$ may also be an oxy derivative or an ether substituted oxy derivative of said groups; A, B and C are each a monovalent aroxy, thioaroxy, diester phosphate, diester pyrophosphate, oxyalkylamino, sulfonyl or carboxyl; and $a+b+c=3$.

2. A composition comprising a comminuted material reacted with a neoalkoxy compound having the formula:

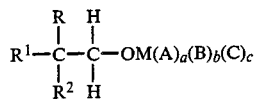

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative or an ether substituted oxy derivative of said groups; A, B and C are each a monovalent aroxy, thioaroxy, diester phosphate, diester pyrophosphate, oxyalkylamino, sulfonyl or carboxyl; and $a+b+c=3$.

3. A polymer composition which comprises a polymer and a neoalkoxy compound having the formula:

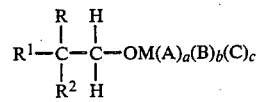

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be oxy derivative of said groups or an ether substituted oxy derivative of said groups; A, B and C are each a monovalent aroxy, thioaroxy, diester phosphate, diester pyrophosphate, oxyalkylamino, sulfonyl or carboxyl; and $a+b+c=3$.

4. A polymeric composition which comprises a polymer, a comminuted material, and a neoalkoxy compound having the formula:

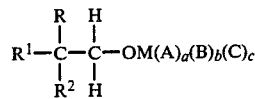

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative or an ether substituted oxy derivative of said groups; A, B and C are each a monovalent aroxy, thioaroxy, diester phosphate, diester pyrophosphate, oxyalkylamino, sulfonyl or carboxyl; and $a+b+c=3$.

5. A process for preparing a polymeric material which comprises compounding in a single step a polymer, a comminuted material and a neoalkoxy compound having the formula:

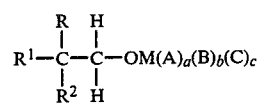

wherein M is titanium or zirconium, R, $R^1$ and $R^2$ are each a monovalent alkyl, alkenyl, alkynyl, aralkyl, aryl or alkaryl group having up to 20 carbon atoms or a halogen or ether substituted derivative thereof, and, in addition, $R^2$ may also be an oxy derivative or an ether substituted oxy derivative of said groups; A, B and C are each a monovalent aroxy, thioaroxy, diester phosphate, diester pyrophosphate, oxyalkylamino, sulfonyl or carboxyl; and $a+b+c=3$.

6. The process of claims 3, 4 or 5 wherein the polymer is a thermoplastic polyester, a polyester, an amide or a polycarbonate.

7. The organo-zirconate of claim 1 wherein R, $R^1$ and $R^2$ are alkyl groups.

8. The organo-zirconate of claim 1 wherein a is equal to 3 and A is an alkyl-substituted carboxyl group.

9. The organo-zirconate of claim 1 wherein a is equal to 3 and A is an alkaryl-substituted sulfonyl group.

10. The organo-zirconate of claim 9 wherein A is a dodecylphenyl group.

11. The organo-zirconate of claim 1 wherein a is equal to 3 and A is a dialkylphosphate group.

12. The organo-zirconate of claim 11 wherein A is a dioctylphosphate group.

13. The organo-zirconate of claim 1 wherein a is equal to 3 and A is a dialkylpyrophosphate group.

14. The organo-zirconate of claim 13 wherein A is a dioctylpyrophosphate group.

15. The organo-zirconate of claim 1 wherein a is equal to 3 and A is an alkylamino group.

16. The organo-zirconate of claim 15 wherein A is an N-ethylaminoethylamino group.

17. The organo-zirconate of claim 1 wherein a is equal to 3 and A is an aminoaryl group.

18. The organo-zirconate of claim 17 wherein A is an aminophenyl group.

* * * * *